United States Patent
Halland et al.

(10) Patent No.: US 8,283,476 B2
(45) Date of Patent: Oct. 9, 2012

(54) TRANSITION METAL CATALYZED SYNTHESIS OF 2H-INDAZOLES

(75) Inventors: Nis Halland, Frankfurt am Main (DE); Marc Nazare, Frankfurt am Main (DE); Andreas Lindenschmidt, Frankfurt am Main (DE); Jorge Alonso, Mannheim (DE); Omar Rkyek, Kassel (DE); Matthias Urmann, Frankfurt am Main (DE)

(73) Assignee: Sanofi, Paris (FR)

( * ) Notice: Subject to any disclaimer, the term of this patent is extended or adjusted under 35 U.S.C. 154(b) by 162 days.

(21) Appl. No.: 12/644,371

(22) Filed: Dec. 22, 2009

(65) Prior Publication Data
US 2010/0234601 A1    Sep. 16, 2010

Related U.S. Application Data

(63) Continuation of application No. PCT/EP2008/004637, filed on Jun. 11, 2008.

(30) Foreign Application Priority Data

Jun. 26, 2007    (EP) .................................... 07290799

(51) Int. Cl.
    *C07D 231/56*    (2006.01)
(52) U.S. Cl. ................... 548/362.5; 548/361.1
(58) Field of Classification Search ............... 548/362.5, 548/361.1
    See application file for complete search history.

(56) References Cited

FOREIGN PATENT DOCUMENTS

WO    WO 99/43643    * 9/1999

OTHER PUBLICATIONS

Dorwald F. A. Side Reactions in Organic Synthesis, 2005, Wiley: VCH, Weinheim p. IX of Preface p. 1-15.*

Steffan, Robert J. et al., "Synthesis and Activity of Substituted 4-(Indazol-4-yl)Phenol as Pathway-Selective Estrogen Receptor Ligands Useful in the Treatment of Rheumatoid Arthritis," Journal of Medicinal Chemistry (2004), vol. 47, pp. 6435-6438.
Song, Jinhua J. et al., "A Novel Synthesis of 2-Aryl-2H-indazoles via a Palladium-Catalyzed Intramolecular Amination Reaction," Organic Letters (2000), vol. 2, No. 4, pp. 519-521.
Cacchi, Sandro et al., "Synthesis of N,N-Dialkyl-N'-arylhydrazines via Palladium-Catalyzed N-Arylation by Using N,N-Dialkylhydrazines/2LiCl Adducts," Organic Letters (2005), vol. 7, No. 8, pp. 1497-1500.
Prikhodko, T.A. et al., "Heterocyclization of o-(arylethynyl)arylhydrazines as a new procedure for the synthesis of substituted 1H- and 2H-indazoles and indoles," Russian Chemical Bulletin, International Edition (2001), vol. 50, No. 7, pp. 1268-1273.
Kamuro, Y. et al., Chemical Regulation of Plants (1982), vol. 17, pp. 65-70.

* cited by examiner

*Primary Examiner* — Nizal Chandrakumar
(74) *Attorney, Agent, or Firm* — Scully, Scott, Murphy & Presser, P.C.

(57) ABSTRACT

The present invention relates to a process for the regioselective synthesis of compounds of the formula I,

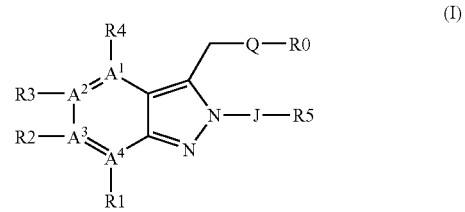

(I)

wherein R0; R1; R2; R3; R4; R5; A1; A2; A3; A4, Q and J have the meanings indicated in the claims. The present invention provides a direct transition metal catalyzed process to a wide variety of multifunctional 2H-indazoles or 2H-azaindazoles of the formula (I) from 2-halo-phenylacetylenes or (2-sulfonato)phenylacetylenes and monosubstituted hydrazines.

1 Claim, No Drawings

TRANSITION METAL CATALYZED SYNTHESIS OF 2H-INDAZOLES

FIELD OF THE INVENTION

The present invention relates to a process for the regioselective synthesis of compounds of the formula (I),

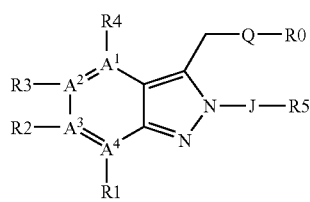

wherein R0, R1, R2, R3, R4, R5, A1, A2, A3, A4, Q and J have the meanings indicated below and are useful as intermediates for the preparation of valuable pharmaceutically active ingredients.

BACKGROUND OF THE INVENTION

The present invention relates to a direct transition metal catalyzed process for the preparation of a variety of multifunctional substituted 2H-indazoles or substituted 2H-azaindazoles of the formula (I) from 2-halo-phenylacetylenes or (2-sulfonato)phenyl-acetylenes and monosubstituted hydrazines.

Indazoles display a vide variety of biological activities and can be regarded as important structures in pharmaceutical research. The ability of the indazole scaffold to mediate an interaction with a variety of biological targets, is well-documented by a number of reports on the observed biological activity, as well as by the fact that several indazole based compounds are in development or marketed as drugs demonstrating that this heterocycle can be an important element of a valuable pharmaceutically active ingredient. Some examples of biological activities include anti-inflammatory activity (R. J. Steffan, E. Matelan, M. A. Ashwell, W. J. Moore, W. R. Solvibile, E. Trybulski, C. C. Chadwick, S. Chippari, T. Kenney, A. Eckert, L. Borges-Marcucci, J. C. Keith, Z. Xu, L. Mosyak, D. C. Harnish *J. Med. Chem.* 2004, 47, 6435-38).

Of course the use of indazoles or azaindoles is not limited to the above-mentioned pharmaceutical application. For example it is well known that indazoles can be useful in numerous other applications, for example as plant growth regulators (Y. Kamuro, K. Hirai *Chemical Regulation of Plants*, 1982, 17, 65) or liquid crystals (C. Canlet, M. A. Khan, B. M. Fung, F. Roussel, P. Judeinstein, J.-P. Bayle *New. J. Chem.* 1999, 23, 1223) among others.

Indazoles exist in 3 isomeric forms as 1H-, 2H- and 3H-indazoles depending on the substitution pattern of the heterocyclic ring and though a number of syntheses have been developed for the formation of 1H-indazoles, no general protocol for the synthesis of 2H-indazoles exist.

Known processes for preparing substituted 2H-indazoles or substituted 2H-aza-indazoles (J. J. Song, N. K. Yee, *Org. Lett.*, Vol. 2, No. 4, 2000, 519-521; L. D. Shirtcliff, T. R. Weakley, M. M. Haley, F. Köhler, R. Herges *J. Org. Chem*, 2004, 69, 6979-85) by direct N-arylation or N-alkylation inevitably yielded a mixture of N(1) and N(2) regioisomers with poor selectivity. The few methods available so far are multi-step processes often affording low yields and regioselectivities with a restricted substrate range and thus a poor cost-effectiveness and therefore of limited use but suffer from the same limitations as the traditional procedures mentioned above. Although numerous transition metal catalyzed protocols for the intermolecular cross-coupling between aryl halides and amides, amines, hydrazides and hydrazones have been reported, only three examples employing hydrazines exist. Buchwald et al. describes several examples of cross-coupling between monosubstituted, 1,1- and 1,2-disubstituted hydrazines with aryl bromides (S. L. Buchwald, S. Wagaw, O. Geis WO99/43643) using a palladium catalyst in toluene and tert-butoxide base to obtain the desired arylated hydrazines in moderate to good yields. A similar catalytic system was reported by Cacchi et al. for the cross-coupling of 1,1-dialkyl-substituted hydrazine-$(LiCl_2)_2$ adducts with aryl bromides in good yields (S. Cacchi, G. Fabrizi, A. Goggiamani, E. Licandro, S. Maiorana, D. Perdicchia *Org. Lett.* 2005, 2, 1497-1500). Vasilevsky and Prikhodko have employed hydrazine in a cross-coupling reaction with (2-chloro-5-nitrophenyl)arylacetylenes to afford 1H-indazoles in good yields (T. A. Prikhodko, S. F. Vasilevsky *Russ. Chem. Bull. Int. Ed.*, 2001, 50, 1268-1273). The reaction proceeds by a palladium catalyzed domino coupling-cyclization reaction and the scope of the reaction is rather limited as only four examples were reported and only (2-chloro-5-nitrophenyl)arylacetylenes were employed. Furthermore, in the same communication Vasilevsky and Prikhodko also report a single example of the palladium catalyzed domino Sonogashira-cyclization reaction of 2-iodoarylhydrazine and 4-nitrophenyl-acetylene to afford 4-nitrobenzyl-1H-indazole in low yield. A single example of 2H-indazole formation in 30% yield by the same domino Sonogashira-cyclization reaction between N'-(2-iodophenyl)acetic hydrazide and 4-nitrophenylacetylene is also described in the report.

It has now been found that the disadvantages mentioned can be avoided by a direct, catalytic, mild, versatile and regioselective synthesis.

The object is achieved by starting from 2-halo-phenylacetylenes or (2-sulfonate)phenyl-acetylenes of formula II and monosubstituted hydrazines of formula III in the presence of a transition metal catalyst.

SUMMARY OF THE INVENTION

The present invention provides a direct transition metal catalyzed synthetic route to a wide variety of multifunctional substituted 2H-indazoles or substituted 2H-azaindazoles of formula I starting from 2-halo-phenylacetylenes or (2-sulfonate)phenylacetylenes of formula II and monosubstituted hydrazines of formula III.

The advantages of the provided process are that it comprises a direct, catalytic, mild and versatile method for the synthesis of substituted 2H-indazoles or substituted 2H-aza-indazoles. Since the multi-step reaction proceeds as a one-pot domino reaction sequence using only a single catalyst, the process is very time- and cost-effective as well as being environmentally benign. Furthermore, the reaction conditions are compatible with a broad range of functional groups and a large variety of starting materials ensuring the generality of the reaction.

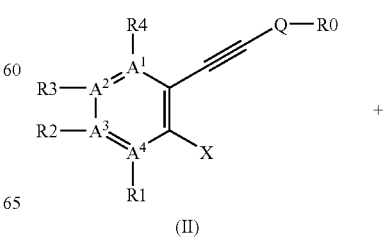

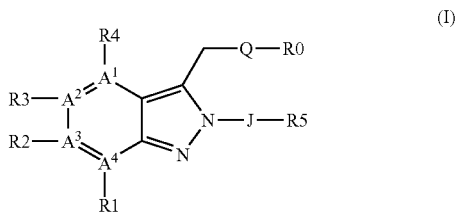

(III) → (I)

DETAILED DESCRIPTION OF THE INVENTION

The invention therefore relates to a process for obtaining the compound of the formula (I)

and/or all stereoisomeric forms of the compound of formula I, and/or mixtures of these forms in any ratio, and/or a physiologically tolerated salt of the compound of formula I, wherein A1, A2, A3 and A4 are independently from each other selected from a carbon or a nitrogen atom to form together with the two carbon atoms in formula I a stable aromatic or heteroaromatic ring;

Q is a covalent bond,
- —$(C_1$-$C_6)$-alkylene, wherein alkylene is unsubstituted or mono-, di- or trisubstituted independently of one another by R14;
- —$(C_3$-$C_8)$-cycloalkyl, wherein cycloalkyl is unsubstituted or mono-, di- or trisubstituted independently of one another by R14;
- —$(C_6$-$C_{14})$-aryl, wherein aryl is unsubstituted or mono-, di-, tri- or four times substituted independently of one another by R13;
- —$(C_1$-$C_4)$-alkylene-O—$(C_1$-$C_4)$-alkylene,
- —$(C_1$-$C_4)$-alkylene-O—; or
- —$(C_5$-$C_{14})$-heteroaryl, wherein heteroaryl is unsubstituted or mono-, di-, tri- or four times substituted independently of one another by R13;

J is a covalent bond,
- —$(C_1$-$C_6)$-alkylene, wherein alkylene is unsubstituted or mono-, di- or trisubstituted independently of one another by R14;
- —$(C_3$-$C_8)$-cycloalkyl, wherein cycloalkyl is unsubstituted or mono-, di- or trisubstituted independently of one another by R14;
- —$(C_6$-$C_{14})$-aryl, wherein aryl is unsubstituted or mono-, di-, tri- or four times substituted independently of one another by R13; or
- —$(C_5$-$C_{14})$-heteroaryl, wherein heteroaryl is unsubstituted or mono-, di-, tri- or four times substituted independently of one another by R13;

R0, R1, R2, R3 and R4 are independent of one another identical or different and are
a) hydrogen atom,
b) —$(C_1$-$C_4)$-alkyl, wherein alkyl is unsubstituted or substituted one to three times by R13,
c) halogen,
d) phenyloxy-, wherein phenyloxy is unsubstituted or substituted one to three times by R13,
e) —$(C_1$-$C_3)$-fluoroalkyl,
f) —N(R10)-$(C_1$-$C_4)$-alkyl, wherein alkyl is unsubstituted or substituted one to three times by R13,
g) —$(C_6$-$C_{14})$-aryl, wherein aryl is unsubstituted or mono-, di-, tri- or four times substituted independently of one another by R13,
h) —$(C_5$-$C_{14})$-heteroaryl, wherein heteroaryl is unsubstituted or mono-, di-, tri- or four times substituted independently of one another by R13,
i) —$(C_3$-$C_8)$-cycloalkyl, wherein said cycloalkyl is unsubstituted or mono-, di-, tri- or four times substituted independently of one another by R13,
j) a 3- to 7-membered cyclic residue, containing 1, 2, 3 or 4 heteroatoms chosen from nitrogen, sulfur or oxygen, wherein said cyclic residue is unsubstituted or mono-, di-, tri- or four times substituted independently of one another by R13,
k) —O—$CF_3$,
l) —O—$(C_1$-$C_4)$-alkyl, wherein alkyl is unsubstituted or substituted one to three times by R13,
m) —$NO_2$,
n) —CN,
o) —OH,
p) —C(O)—R10,
q) —C(O)—O—R11,
r) —C(O)—N(R11)-R12,
s) —N(R11)-R12,
t) —N(R10)-$SO_2$—R10,
u) —S—R10,
v) —$SO_n$—R10, wherein n is 1 or 2,
w) —$SO_2$—N(R11)-R12, or
x) —O—$SO_2$—R13, or
y) at least one of R1, R2, R3 or R4 are absent in case one or more of A1, A2, A3 or A4 are nitrogen atom, or
R1 and R2, R2 and R3 or R3 and R4 form together with the atoms which they are attached to a 5- or 8-membered ring, containing up to 0, 1, 2, 3 or 4 heteroatoms chosen from nitrogen, sulfur or oxygen, wherein said ring is unsubstituted or substituted one, two, three or four times by R14, R5 is a) —$(C_1$-$C_4)$-alkyl, wherein alkyl is unsubstituted or substituted one to three times by R13,
b) halogen,
c) phenyloxy-, wherein phenyloxy is unsubstituted or substituted one to three times by R13,
d) —$(C_1$-$C_3)$-fluoroalkyl,
e) —N(R10)-$(C_1$-$C_4)$-alkyl, wherein alkyl is unsubstituted or substituted one to three times by R13,
f) —$(C_6$-$C_{14})$-aryl, wherein aryl is unsubstituted or mono-, di-, tri- or four times substituted independently of one another by R13,
g) —$(C_5$-$C_{14})$-heteroaryl, wherein heteroaryl is unsubstituted or mono-, di-, tri- or four times substituted independently of one another by R13,
h) —$(C_3$-$C_8)$-cycloalkyl, wherein said cycloalkyl is unsubstituted or mono-, di-, tri- or four times substituted independently of one another by R13,
i) a 3- to 7-membered cyclic residue, containing 1, 2, 3 or 4 heteroatoms chosen from nitrogen, sulfur or oxygen, wherein said cyclic residue is unsubstituted or mono-, di-, tri- or four times substituted independently of one another by R13,
j) —O—$CF_3$,
k) —O—$(C_1$-$C_4)$-alkyl, wherein alkyl is unsubstituted or substituted one to three times by R13,
l) —$NO_2$,
m) —CN,
n) —OH, o) —C(O)—R10,
p) —C(O)—O—R11,
q) —C(O)—N(R11)-R12,
r) —N(R11)-R12,
s) —N(R10)-SO$_2$—R10,
t) —S—R10,
u) —SO$_n$—R10, wherein n is 1 or 2,
v) —SO$_2$—N(R11)-R12, or
w) —O—SO$_2$—R13, R10 is hydrogen atom, —(C$_1$-C$_3$)-fluoroalkyl or —(C$_1$-C$_6$)-alkyl, R11 and R12 are independently of one another identical or different and are
  a) hydrogen atom,
  b) —(C$_1$-C$_6$)-alkyl, wherein alkyl is unsubstituted or mono-, di- or trisubstituted independently of one another by R13,
  c) —(C$_6$-C$_{14}$)-aryl-, wherein aryl is unsubstituted or mono-, di- or trisubstituted independently of one another by R13, or
  d) —(C$_5$-C$_{14}$)-heteroaryl, wherein heteroaryl is unsubstituted or mono-, di- or trisubstituted independently of one another by R13, R13 is halogen, —NO$_2$, —CN, =O, —OH, —(C$_1$-C$_8$)-alkyl, —(C$_1$-C$_8$)-alkoxy, —CF$_3$, phenyloxy-, —C(O)—R10, —C(O)—O—R17, —C(O)—N(R17)-R18, —N(R17)-R18, —N(R10)-SO$_2$—R10, —S—R10, —SO$_n$—R10, wherein n is 1 or 2, —SO$_2$—N(R17)-R18, —(C$_9$-C$_{14}$)-aryl, wherein aryl is unsubstituted or mono-, di- or trisubstituted independently of one another by R14, —(C$_5$-C$_{14}$)-heteroaryl, wherein heteroaryl is unsubstituted or mono-, di- or trisubstituted independently of one another by R14, —(C$_3$-C$_8$)-cycloalkyl, wherein said cycloalkyl is unsubstituted or mono-, di- or trisubstituted independently of one another by R14, or a 3- to 7-membered cyclic residue, containing up to 1, 2, 3 or 4 heteroatoms chosen from nitrogen, sulfur or oxygen, wherein said cyclic residue is unsubstituted or mono-, di- or trisubstituted independently of one another by R14, R14 is halogen, —OH, =O, —CN, —CF$_3$, —(C$_1$-C$_8$)-alkyl, —(C$_1$-C$_4$)-alkoxy, —NO$_2$, —C(O)—OH, —N(R11)-R12, —C(O)—O—(C$_1$-C$_4$)-alkyl, —(C$_1$-C$_8$)-alkylsulfonyl, —C(O)—NH—(C$_1$-C$_8$)-alkyl, —C(O)—N[(C$_1$-C$_8$)-alkyl]$_2$, —C(O)—NH$_2$, —S—R10, —N(R10)-C(O)—NH—(C$_1$-C$_8$)-alkyl, or —N(R10)-C(O)—N[(C$_1$-C$_8$)-alkyl]$_2$, R17 and R18 are independently of one another identical or different and are
  a) hydrogen atom,
  b) —(C$_1$-C$_6$)-alkyl,
  c) —(C$_6$-C$_{14}$)-aryl- or
  d) —(C$_5$-C$_{14}$)-heteroaryl, said process comprises reacting a compound of formula II

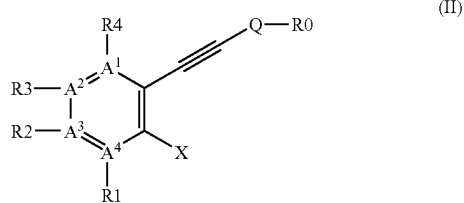

wherein R0, R1, R2, R3, R4, A1, A2, A3, A4 and Q are as defined in formula I and X is Cl, Br, I, triflate, nonaflate, tosylate, alkyl sulfonate or aryl sulfonate, with a compound of formula III or any salts thereof,

wherein J and R5 are as defined in formula I,
in the presence of a transition metal catalyst to give a compound of formula I and optionally the compound of formula I is converted to its physiologically tolerated salt.

2) The present invention also relates to a process for the preparation of a compound of formula I, wherein
A1, A2, A3 and A4 form together with the two carbon atoms in formula I a benzene, pyrazine, pyridazine, pyridine, pyrimidine, triazine or tetrazine,
Q is a covalent bond,
  —(C$_1$-C$_6$)-alkylene, wherein alkylene is unsubstituted or mono-, di- or trisubstituted independently of one another by R14;
  —(C$_3$-C$_6$)-cycloalkyl, wherein cycloalkyl is unsubstituted or mono-, di- or trisubstituted independently of one another by R14;
  phenyl, wherein phenyl is unsubstituted or mono-, di-, tri- or four times substituted independently of one another by R13;
  —(C$_1$-C$_4$)-alkylene-O—(C$_1$-C$_4$)-alkylene,
  —(C$_1$-C$_4$)-alkylene-O—, or
  —(C$_5$-C$_{14}$)-heteroaryl, wherein heteroaryl is selected from acridinyl, azaindole (1H-pyrrolopyridinyl), azabenzimidazolyl, azaspirodecanyl, azepinyl, azetidinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxazolinyl, dioxazolyl, dioxazinyl, 1,3-dioxolanyl, 1,3-dioxolenyl, 3,3-dioxo[1,3,4]oxathiazinyl, 6H-1,5,2-dithiazinyl, dihydrofuro[2,3-b]-tetrahydrofuranyl, furanyl, furazanyl, imidazolidinyl, imidazolinyl, imidazolyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxathiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyrazolo[3,4-b]pyridine, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrahydrofuranyl, tetrahydropyranyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl, and wherein heteroaryl is unsubstituted or mono-, di-, tri- or four times substituted independently of one another by R13;

J is a covalent bond,
—($C_1$-$C_6$)-alkylene, wherein alkylene is unsubstituted or mono-, di- or trisubstituted independently of one another by R14;
—($C_3$-$C_6$)-cycloalkyl, wherein cycloalkyl is unsubstituted or mono-, di- or trisubstituted independently of one another by R14;
phenyl, wherein phenyl is unsubstituted or mono-, di-, tri- or four times substituted independently of one another by R13; or
—($C_5$-$C_{14}$)-heteroaryl, wherein heteroaryl is as defined above and is unsubstituted or mono-, di-, tri- or four times substituted independently of one another by R13;

R0, R1, R2, R3 and R4 are independent of one another identical or different and are
a) hydrogen atom,
b) —($C_1$-$C_4$)-alkyl, wherein alkyl is unsubstituted or substituted one, two or three times by R13,
c) F, Cl or Br,
d) phenyloxy-, wherein phenyloxy is unsubstituted or substituted one, two or three times by R13,
e) —($C_1$-$C_3$)-fluoroalkyl,
f) —N(R10)-($C_1$-$C_4$)-alkyl, wherein alkyl is unsubstituted or substituted one, two or three times by R13,
g) phenyl or naphthyl, wherein phenyl or naphthyl are unsubstituted or substituted one, two or three times by R13,
h) —($C_5$-$C_{14}$)-heteroaryl, wherein heteroaryl is as defined above and is unsubstituted or mono-, di-, tri- or four times substituted independently of one another by R13,
i) —($C_3$-$C_8$)-cycloalkyl, wherein said cycloalkyl is unsubstituted or mono-, di-, tri- or four times substituted independently of one another by R13,
j) a 3- to 7-membered cyclic residue selected from azepine, azetidine, aziridine, azirine, 1,4-diazepane, 1,2-diazepine, 1,3-diazepine, 1,4-diazepine, diaziridine, diazirine, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketomorpholine, ketopiperazine, morpholine, 1,2-oxa-thiepane, 1,2-oxathiolane, 1,4-oxazepane, 1,2-oxazine, 1,3-oxazine, 1,4-oxazine, oxazole, oxaziridine, oxetan, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydrofuran, tetrahydropyran, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole, and is unsubstituted or mono-, di-, tri- or four times substituted independently of one another by R13,
k) —O—$CF_3$,
l) —O—($C_1$-$C_4$)-alkyl, wherein alkyl is unsubstituted or substituted one, two or three times by R13,
m) —CN,
n) —OH,
o) —C(O)—R10
p) —C(O)—O—R11,
q) —C(O)—N(R11)-R12,
r) —N(R11)-R12,
s) —N(R10)-$SO_2$—R10,
t) —S—R10,
u) —$SO_n$—R10, wherein n is 1 or 2,
v) —$SO_2$—N(R11)-R12, or
w) —O—$SO_2$—R13, or
x) at least one of R1, R2, R3 or R4 are absent in case one or more of A1, A2, A3 or A4 are nitrogen atom, R5 is a) —($C_1$-$C_4$)-alkyl, wherein alkyl is unsubstituted or substituted one, two or three times by R13,
b) F, Cl or Br,
c) phenyloxy-, wherein phenyloxy is unsubstituted or substituted one, two or three times by R13,
d) —($C_1$-$C_3$)-fluoroalkyl,
e) —N(R10)-($C_1$-$C_4$)-alkyl, wherein alkyl is unsubstituted or substituted one, two or three times by R13,
f) phenyl or naphthyl, wherein phenyl or naphthyl are unsubstituted or substituted one, two or three times by R13,
g) —($C_5$-$C_{14}$)-heteroaryl, wherein heteroaryl is as defined above and is unsubstituted or mono-, di-, tri- or four times substituted independently of one another by R13,
h) —($C_3$-$C_8$)-cycloalkyl, wherein said cycloalkyl is unsubstituted or mono-, di-, tri- or four times substituted independently of one another by R13,
i) a 3- to 7-membered cyclic residue selected from azepine, azetidine, aziridine, azirine, 1,4-diazepane, 1,2-diazepine, 1,3-diazepine, 1,4-diazepine, diaziridine, diazirine, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketomorpholine, ketopiperazine, morpholine, 1,2-oxa-thiepane, 1,2-oxathiolane, 1,4-oxazepane, 1,2-oxazine, 1,3-oxazine, 1,4-oxazine, oxazole, oxaziridine, oxetan, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydrofuran, tetrahydropyran, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole, and is unsubstituted or mono-, di-, tri- or four times substituted independently of one another by R13,
j) —O—$CF_3$,
k) —O—($C_1$-$C_4$)-alkyl, wherein alkyl is unsubstituted or substituted one, two or three times by R13,
l) —CN,
m) —OH,
n) —C(O)—R10
o) —C(O)—O—R11,
p) —C(O)—N(R11)-R12,
q) —N(R11)-R12,
r) —N(R10)-$SO_2$—R10,
s) —S—R10,
t) —$SO_n$—R10, wherein n is 1 or 2,
u) —$SO_2$—N(R11)-R12, or
v) —O—$SO_2$—R13, R10 is hydrogen atom, —($C_1$-$C_3$)-fluoroalkyl or —($C_1$-$C_6$)-alkyl, R11 and R12 are independently of one another identical or different and are
  a) hydrogen atom,
  b) —($C_1$-$C_4$)-alkyl, wherein alkyl is unsubstituted or mono-, di- or trisubstituted independently of one another by R13,
  c) phenyl, wherein phenyl is unsubstituted or mono-, di- or trisubstituted independently of one another by R13,
  d) —($C_5$-$C_{14}$)-heteroaryl, wherein heteroaryl is as defined above and is unsubstituted or mono-, di- or trisubstituted independently of one another by R13, R13 is F, Cl, —CN, =O, —OH, —($C_1$-$C_8$)-alkyl, —($C_1$-$C_8$)-alkoxy, —$CF_3$, phenyloxy-, —C(O)—R10, —C(O)—O—R17, —C(O)—N(R17)-R18, —N(R17)-R18, —N(R10)-$SO_2$—R10, —S—R10, —$SO_n$—R10, wherein n is 1 or 2, —$SO_2$—N(R17)-R18, phenyl, wherein phenyl is unsubstituted or mono-, di- or trisubstituted independently of one another by R14, —($C_5$-$C_{14}$)-heteroaryl, wherein heteroaryl is as defined above and is unsubstituted or mono-, di- or trisubstituted independently of one another by R14, —($C_3$-$C_6$)-cycloalkyl, wherein said cycloalkyl is unsubstituted or mono-, di- or trisubstituted independently of one another by R14, or a 3- to 7-membered cyclic residue, which is as defined above and is unsubstituted or mono-, di- or trisubstituted independently of one another by R14, R14 is F, Cl, —OH, =O, —CN, —$CF_3$, —($C_1$-$C_8$)-alkyl, —($C_1$-$C_4$)-alkoxy, —C(O)—OH, —N(R11)-R12, —C(O)—O—($C_1$-$C_4$)-alkyl, —($C_1$-$C_8$)-alkylsulfonyl, —C(O)—$NH_2$, —C(O)—NH—($C_1$-$C_8$)-alkyl, —C(O)—N[($C_1$-$C_8$)-alkyl]$_2$, —S—R10, —N(R10)-C(O)—NH—($C_1$-$C_8$)-alkyl or —N(R10)-C(O)—N[($C_1$-$C_8$)-alkyl]$_2$, R17 and R18 are independently of one another identical or different and are
  a) hydrogen atom,
  b) —($C_1$-$C_4$)-alkyl,
  c) phenyl or
  d) —($C_5$-$C_{14}$)-heteroaryl, wherein heteroaryl is as defined above, and X is Cl, Br, I, triflate, nonaflate, tosylate, alkyl sulfonate or aryl sulfonate.

3) The present invention also relates to a process for the preparation of a compound of formula I, wherein
A1, A2, A3 and A4 form together with the two carbon atoms in formula I a benzene or pyridine,
Q is a covalent bond,
  —($C_1$-$C_6$)-alkylene,
  —($C_3$-$C_6$)-cycloalkyl,
  phenyl, wherein phenyl is unsubstituted or mono-, di-, tri- or four times substituted independently of one another by R13,
  —($C_1$-$C_4$)-alkylene-O—($C_1$-$C_4$)-alkylene,
  —($C_1$-$C_4$)-alkylene-O—; or
  —($C_5$-$C_{14}$)-heteroaryl, wherein heteroaryl is selected from pyridyl, quinolinyl, tetrahydropyranyl and thienyl,
J is a covalent bond, —($C_1$-$C_6$)-alkylene, —($C_3$-$C_6$)-cycloalkyl, phenyl, naphthyl, or —($C_5$-$C_{14}$)-heteroaryl, wherein heteroaryl is as defined above,
R0, R1, R2, R3 and R4 are independent of one another identical or different and are
  a) hydrogen atom,
  b) —($C_1$-$C_4$)-alkyl, wherein alkyl is unsubstituted or substituted one, two or three times by R13,
  c) F, Cl or Br,
  d) naphthyl, wherein naphthyl is unsubstituted or substituted one, two or three times by R13,
  e) phenyl, wherein phenyl is unsubstituted or substituted one, two or three times by R13,
  f) —($C_5$-$C_{14}$)-heteroaryl, wherein heteroaryl is as defined above,
  g) —($C_3$-$C_6$)-cycloalkyl,
  h) —O—($C_1$-$C_4$)-alkyl,
  i) —CN,
  j) —OH,
  k) —C(O)—R10,
  l) —C(O)—O—R11,
  m) —C(O)—N(R11)-R12,
  n) —N(R11)-R12, or
  p) —O—$SO_2$—R13, R5 is a) —($C_1$-$C_4$)-alkyl, wherein alkyl is unsubstituted or substituted one, two or three times by R13,
  b) F, Cl or Br,
  c) naphthyl, wherein naphthyl is unsubstituted or substituted one, two or three times by R13,
  d) phenyl, wherein phenyl is unsubstituted or substituted one, two or three times by R13,
  e) —($C_5$-$C_{14}$)-heteroaryl, wherein heteroaryl is as defined above,
  f) —($C_3$-$C_6$)-cycloalkyl,
  g) —O—($C_1$-$C_4$)-alkyl,
  h) —CN,
  i) —OH,
  j) —C(O)—R10,
  k) —C(O)—O—R11,
  l) —C(O)—N(R11)-R12,
  m) —N(R11)-R12, or
  n) —O—$SO_2$—R13, R10 is hydrogen atom or —($C_1$-$C_4$)-alkyl, R11 and R12 are independently of one another identical or different and are hydrogen atom or —($C_1$-$C_4$)-alkyl, wherein alkyl is unsubstituted or mono-, di- or trisubstituted independently of one another by R13, R13 is F, Cl, —CN, —OH, —($C_1$-$C_4$)-alkoxy, —$CF_3$ or phenyl, wherein phenyl is unsubstituted or mono-, di- or trisubstituted independently of one another by R14, R14 is F, Cl, —OH, —CN, —$CF_3$, —($C_1$-$C_4$)-alkyl or —($C_1$-$C_4$)-alkoxy, and X is Cl, Br, I or tosylate.

The reaction can be performed in a broad range of protic or aprotic solvents, including polar aprotic solvents, or even in some cases without a solvent. Examples of said solvents are: tert-butanol, benzene, toluene, xylene, mesitylene, acetonitrile, propionitrile, tetrahydrofurane, 2-methyl-tetrahydrofurane, N,N-dimethylformamide, N-methylpyrrolidinone, N,N-dimethylacetamide, dimethylsulfoxide, 1,2-dimethoxyethane, tert-butylmethylether, triethylamine, diisopropylethylamine or pyridine. Preferred is N,N-dimethylacetamide, N,N-dimethylformamide, N-methylpyrrolidinone. Most preferred is N,N-dimethylformamide.

Useful bases for the process of the present invention is a basic organic or inorganic compound that acts as proton acceptor without inhibiting the catalytic activity of the employed transition metal catalyst. Suitable classes of such bases are for example carbonates, phosphates, alkoxides, hydroxides, amides, hydrides with a suitable metal as counter ion, or an alkali metal. Carbonates and phosphates are the preferred bases in the process of the present invention. Potassium carbonate or potassium phosphate and in particular cesium carbonate are the preferred bases. The bases can be used in pure form or a mixture of several bases can be used.

The bases are generally employed in moderate excess based on 2-halo-phenylacetylenes or (2-sulfonate)phenylacetylenes of formula II. A useful range is a 0.5 to 10 fold excess based on the 2-halo-phenylacetylenes or (2-sulfonate) phenyl-acetylenes of formula II. An even more useful range 1.1-2.0 fold excess based on the 2-halo-phenylacetylenes or (2-sulfonate)phenylacetylenes of formula II. The base may be favourably employed in a 1.4 fold excess based on the 2-halo-phenylacetylenes or (2-sulfonate)phenylacetylenes of formula II. In reactions where the hydrazine is employed as a salt, e.g. as a hydrochloride salt, one additional equivalent of base compared to the salt is added is added to the reaction mixture in order to generate the hydrazine in situ. Alternatively, the reaction can also be performed without a base if the hydrazine is used as the corresponding amide prepared by reaction of the hydrazine or hydrazine salt with a strong base. The active form of the transition metal catalyst is not known. Therefore, the term "transition metal catalyst" in the present invention shall include any catalytic transition metal and/or catalyst precursor introduced into the reaction vessel and converted in situ into the active form, as well as the active form of the catalyst that promotes any part of the reaction. The transition metal catalyst can be used in any amount, but generally 0.00005-90 mol % would be employed. Preferred is the use of 0.01-20 mol %, and even more preferred is the use of 0.5-10 mol % and most preferably 1-5 mol % of the transition metal catalyst is employed.

Generally, any suitable transition metal catalyst that can mediate the reaction can be employed these include the elements of group 3-12 of the periodic table as well as the lanthanides. Preferred transition metals include platinum, palladium, nickel, gold, copper, iron, ruthenium, rhodium and iridium. Even more preferred are nickel and palladium and most preferred palladium. The transition metal catalyst can be soluble or insoluble, and the particular source of the transition metal useful in this process can be, but are not limited to: Pd-halides, Pd-halide complexes, Ni-halides, Ni-halide complexes, Pd-phosphine complexes, Ni-phosphine complexes, Pd-alkene complexes, Ni-alkene complexes, Pd-alkanoates, Pd-alkanoate complexes, Pd-acetonates, Ni-alkanoates, Ni-alkanoate complexes, Ni-acetonates, Raney nickel, Pd/C or Ni/C, or polymer supported palladium or nickel species or a mixture thereof. Representative examples include, but are not limited to: palladium (II) chloride, palladium (II) bromide, palladium (II) iodide, tris(dibenzylideneacetone)dipalladium (0), palladium (II) acetate, palladium (II) trifluoroacetate, tris(dibenzylideneacetone)dipalladium(0) chloroform adduct, bis(dibenzylideneacetone)palladium (0), bis(triphenylphosphine)palladium (II) chloride, tetrakis(triphenylphosphine)palladium (0), nickel (II) chloride, nickel (II) bromide, nickel (II) iodide, Ni(acac)$_2$, Ni(1,5-cyclooctadiene)$_2$, acetato(2'-di-tert-butylphosphino-1,1'-biphenyl-2-yl)palladium(II), (1,2-Bis(diphenylphosphino)ethane)di-chloropalladium(II), Bis[1,2-bis(diphenylphosphino)ethane] palladium (0), [(2S,3S)-Bis(diphenylphosphino)butane] [eta3-allyl]palladium(II) perchlorate, 1,3-bis(2,4,6-trimethylphenyl)imidazol-2-ylidene(1,4-naphthoquinone) palladium (0) dimmer, 2,2'-bis(diphenylphosphino)-1,1'-binaphthylpalladium(II) chloride.

The preferred transition metal sources are palladium (II) chloride, palladium (II) bromide, palladium (II) iodide, tris (dibenzylideneacetone)dipalladium(0), palladium (II) acetate, palladium (II) trifluoroacetate, tris(dibenzylideneacetone)dipalladium(0) chloroform adduct, bis(dibenzylideneacetone)palladium (0), bis(triphenylphosphine)-palladium (II) chloride, tetrakis(triphenylphosphine)palladium (0), and even more preferred are palladium (II) chloride, palladium (II) bromide, palladium (II) iodide, tris(dibenzylideneacetone)dipalladium(0). The most preferred palladium sources being palladium (II) chloride and tris(dibenzylideneacetone)dipalladium(0).

The group of ligands useful in this process may be chelating or non-chelating and may include alkyl or aryl phosphines or hybrids thereof e.g. dicyclohexlphenylphosphine, or aryl or alkyl diphospines or hybrids thereof, diamines, imines, heterocyclic carbenes or hybrids thereof.

The ligand can be used in its free form or as a salt, e.g. the hydrochloride or tetrafluoroborate salt.

By way of example only, the ligand can be selected from the following compounds, but are not limited to: tri-tert-butylphosphine, tri-tert-butylphosphine tetrafluoroborate salt, tricyclohexylphosphine, dicyclohexlphenylphosphine, methyldiphenylphosphine, dimethylphenylphosphine, trimethylphosphine, triethylphosphine, triphenylphosphine, 2-dicyclohexylphosphino-2',4',6'-triisopropyl-1,1'-biphenyl, 2,2'-bis(di-tert-butylphosphino)biphenyl, (+/−)-2,2'-bis(diphenylphosphino)-1,1'-binaphthalene, (9,9-dimethyl-9h-xanthene-4,5-diyl)bis[diphenyl phosphine], (R)-(−)-1-[(S)-2-(diphenylphosphino)ferrocenyl] ethyldicyclohexylphosphine, 1,2-bis(diphenylphosphino) ethane, 1,3-bis(diphenylphosphino)propane, (R)-(−)-1-[(S)-2-(dicyclohexylphosphino)ferrocenyl]-ethyldi-tert-butylphosphine, (R)-(+)-1,1'-bis(diphenylphosphino)-2,2'-bis(N,N-diiisopropylamido)ferrocene, (S,S)-1-[1-(di-tert-butylphosphino)ethyl]-2-(diphenylphosphino)ferrocene, (1R,2R)-(+)-1,2-diaminocyclohexane-N,N'-bis(2-diphenylphosphino-1-napthoyl, (−)-1,2-bis((2S,5S)-2,5-diisopropylphospholano)-benzene, bis[(2-diphenylphosphino)phenyl]ether, (S)-(−)-2,2'-Bis(di-para-tolylphosphino)-1,1'-binaphyl, 4,5-bis(bis(3,5-bis(trifluoromethyl)phenyl)-phosphino)-9,9-dimethylxanthen.

Preferred ligands are tri-tert-butylphosphine, tri-tert-butylphosphine tetrafluoroborate salt, tricyclohexylphosphine, 2-dicyclohexylphosphino-2',4',6'-triisopropyl-1,1'-biphenyl. More preferred ligands are tri-tert-butylphosphine, tri-tert-butylphosphine tetrafluoroborate salt, and most preferred is tri-tert-butylphosphine tetrafluoroborate salt.

Most favourably tri-tert-butylphosphine or tri-tert-butylphosphine tetrafluoroborate are employed in particular in combination with a palladium source bearing no phosphine itself, like e.g. palladium (II) chloride, palladium (II) bromide, palladium (II) iodide, or tris(dibenzylideneacetone) dipalladium(0).

The ligand can be used in any amount, but generally 0.00005-90 mol % would be employed. Preferred is the use of 0.01-40 mol %, and even more preferred is the use of 0.5-20 mol % and most preferably 1-10 mol % of the ligand is employed. The ratio of the ligand to the transition metal is generally about 1 to 20, preferably about 1-5 and most preferably 2.

The reaction step is usually carried out in the temperature range 0° C. to 300° C., preferably between 25° C. to 150° C., and most preferably between 80° C. to 130° C. Usually the reaction is carried out under the exclusion of air and moisture such as under an inert atmosphere like e.g. in an argon or nitrogen atmosphere at atmospheric pressure. The reaction time is normally in the range of 2 to 48 hours (h).

The progress of the reaction may be monitored by methods known to those skilled in the art, like for example thin layer silica gel chromatography, gas chromatography, nuclear magnetic resonance, infrared spectroscopy, and high pressure liquid chromatography combined with ultraviolet detection or mass spectroscopy. Preferably thin layer silica gel chromatography and high pressure liquid chromatography (HPLC) combined with mass spectroscopy are used.

The isolation and purification procedures useful for the compounds obtained by the process of the present invention are well-known to those skilled in the art, like for example filtration through a celite containing cartridge, aqueous workup, extraction with organic solvents, distillation, crystallisation, chromatography on silica, and high pressure liquid chromatography on normal phase or reversed phase. Preferred methods include, but are not limited to those exemplified.

The term alkyl as used herein expressly includes saturated groups as well as unsaturated groups which latter groups contain one or more, for example one, two or three, double bonds and/or triple bonds. All these statements also apply if an alkyl group occurs as a substituent on another residue, for example in an alkyloxy residue, an alkyloxycarbonyl residue or an arylalkyl residue. Examples of "—$(C_1-C_8)$-alkyl" or "—$(C_1-C_8)$-alkylene" are alkyl residues containing 1, 2, 3, 4, 5, 6, 7 or 8 carbon atoms are methyl, methylene, ethyl, ethylene, propyl, propylene, butyl, butylene, pentyl, pentylene, hexyl, heptyl or octyl, the n-isomers of all these residues, isopropyl, isobutyl, 1-methylbutyl, isopentyl, neopentyl, 2,2-dimethylbutyl, 2-methylpentyl, 3-methylpentyl, isohexyl, sec-butyl, tBu, tert-pentyl, sec-butyl, tert-butyl or tert-pentyl. Unsaturated alkyl residues are e.g. alkenyl residues such as vinyl, 1-propenyl, 2-propenyl (=allyl), 2-butenyl, 3-butenyl, 2-methyl-2-butenyl, 3-methyl-2-butenyl, 5-hexenyl or 1,3-pentadienyl, or alkynyl residues such as ethynyl, 1-propynyl, 2-propynyl (=propargyl) or 2-butynyl.

The term "—$(C_3-C_8)$-cycloalkyl" is understood as cyclic alkyl residues which contain 3, 4, 5, 6, 7 or 8 ring carbon atoms like cyclopropyl, cyclobutyl, cyclopentyl, cyclohexyl, cycloheptyl or cyclooctyl, which can also be substituted and/or unsaturated. Unsaturated cyclic alkyl groups and unsaturated cycloalkyl groups like, for example, cyclopentenyl or cyclohexenyl can be bonded via any carbon atom.

The term "alkyl sulfonate" is understood as an alkyl residue containing 1, 2, 3, 4, 5 or 6 carbon atoms substituted by sulfonate. Examples of such residues are methylsulfonate (mesylate), ethylsulfonate, propylsulfonate, butylsulfonate, pentylsulfonate or hexylsulfonate.

The term "A1, A2, A3, A4 are independently from each other selected from carbon or nitrogen atoms to form together with the two carbon atoms in formula I a stable aromatic or heteroaromatic ring" refers to a residue which is e.g. selected from benzene, pyrazine, pyridazine, pyridine, pyrimidine, triazine or tetrazine.

The term "—$(C_6-C_{14})$-aryl" is understood as meaning aromatic hydrocarbon radicals containing from 6 to 14 carbon atoms in the ring. Examples of —$(C_6-C_{14})$-aryl radicals are phenyl, naphthyl, for example 1-naphthyl and 2-naphthyl, biphenylyl, for example 2-biphenylyl, 3-biphenylyl and 4-biphenylyl, anthryl or fluorenyl. Biphenylyl radicals, naphthyl radicals and, in particular, phenyl radicals are preferred aryl radicals.

The term "aryl sulfonate" is understood as an aryl as defined herein, which is substituted by a sulfonate. Examples of such compounds are benzenesulfonate, tosylate, nitrobenzenesulfonate or bromobenzenesulfonate.

The term "—$(C_5-C_{14})$-heteroaryl" refers to mono-, di- or tri-ring systems, wherein one or more of the 5 to 14 ring carbon atoms are replaced by heteroatoms such as nitrogen, oxygen or sulfur. Examples are acridinyl, azaindole (1H-pyrrolopyridinyl), azabenz-imidazolyl, azaspirodecanyl, azepinyl, azetidinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxazolinyl, dioxazolyl, dioxazinyl, 1,3-dioxolanyl, 1,3-dioxolenyl, 3,3-dioxo[1,3,4]oxathiazinyl, 6H-1,5,2-dithiazinyl, dihydrofuro[2,3-b]-tetrahydrofuranyl, furanyl, furazanyl, imidazolidinyl, imidazolinyl, imidazolyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyrazolo[3,4-b]pyridine, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrahydrofuranyl, tetrahydropyranyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl.

The term "a 3- to 7-membered cyclic residue, containing 1, 2, 3 or 4 heteroatoms" refer to structures of heterocycles, which are selected from compounds such as azepine, azetidine, aziridine, azirine, 1,4-diazepane, 1,2-diazepine, 1,3-diazepine, 1,4-diazepine, diaziridine, diazirine, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketomorpholine, ketopiperazine, morpholine, 1,2-oxa-thiepane, 1,2-oxathiolane, 1,4-oxazepane, 1,2-oxazine, 1,3-oxazine, 1,4-oxazine, oxazole, oxaziridine, oxetan, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydrofuran, tetrahydropyran, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole.

The term "R1 and R2, R2 and R3 or R3 and R4 form together with the atoms which they are attached to a 5- or 8-membered ring, containing up to 0, 1, 2, 3 or 4 heteroatoms chosen from nitrogen, sulfur or oxygen" refers to residues which are selected from compounds such as azepine, azirine, azocane, azocane-2-one, cycloheptyl, cyclohexyl, cyclooctane, cyclooctene, 1,4-diazepane, 1,2-diazepine, 1,3-diazepine, 1,4-diazepine, [1,2]diazocan-3-one, [1,3]diazocan-2-one, [1,4]diazocane, dioxazine, dioxazole, [1,4]dioxocane, 1,3-dioxolane, dioxole, 1,3-dioxolene, furan, imidazole, imidazolidine, imidazoline, isothiazole, isothiazolidine, isothiazoline, isothiazole, isoxazole, isoxazolidine, isoxazoline, 2-isoxazoline, ketomorpholine, ketopiperazine, morpholine, 1,2-oxa-thiepane, 1,2-oxathiolane, 1,4-oxazepane, 1,2-oxazine, 1,3-oxazine, 1,4-oxazine, oxaziridine, [1,4]oxazocane,

[1,3]oxazocan-2-one, oxocane, oxocan-2-one, oxazole, piperidine, piperazine, phenyl, pyridazine, pyridine, pyrimidine, pyran, pyrazine, pyrazole, pyrazolepyrrole, pyrazolidine, pyrazoline, pyridazine, pyridine, pyrimidine, pyrrole, pyrrolidine, pyrrolidinone, pyrroline, 5,6,7,8-tetrahydro-1H-azocin-2-one, tetrahydrofuran, tetrahydropyran, tetrahydropyridine, tetrazine, tetrazole, thiadiazine, thiadiazole, 1,2-thiazine, 1,3-thiazine, 1,4-thiazine, thiazole, 1,3-thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole.

The term "—($C_1$-$C_3$)-fluoroalkyl" is a partial or totally fluorinated alkyl-residue, which can be derived from residues such as —$CF_3$, —$CHF_2$, —$CH_2F$, —CHF—$CF_3$, —CHF—$CHF_2$, —CHF—$CH_2F$, —$CH_2$—$CF_3$, —$CH_2$—$CHF_2$, —$CH_2$—$CH_2F$, —$CF_2$—$CF_3$, —$CF_2$—$CHF_2$, —$CF_2$—$CH_2F$, —$CH_2$—CHF—$CF_3$, —$CH_2$—CHF—$CHF_2$, —$CH_2$—CHF—$CH_2F$, —$CH_2$—$CH_2$—$CF_3$, —$CH_2$—$CH_2$—$CHF_2$, —$CH_2$—$CH_2$—$CH_2F$, —$CH_2$—$CF_2$—$CF_3$, —$CH_2$—$CF_2$—$CHF_2$, —$CH_2$—$CF_2$—$CH_2F$, —CHF—CHF—$CF_3$, —CHF—CHF—$CHF_2$, —CHF—CHF—$CH_2F$, —CHF—$CH_2$—$CF_3$, —CHF—$CH_2$—$CHF_2$, —CHF—$CH_2$—$CH_2F$, —CHF—$CF_2$—$CF_3$, —CHF—$CF_2$—$CHF_2$, —CHF—$CF_2$—$CH_2F$, —$CF_2$—CHF—$CF_3$, —$CF_2$—CHF—$CHF_2$, —$CF_2$—CHF—$CH_2F$, —$CF_2$—$CH_2$—$CF_3$, —$CF_2$—$CH_2$—$CHF_2$, —$CF_2$—$CH_2$—$CH_2F$, —$CF_2$—$CF_2$—$CF_3$, —$CF_2$—$CF_2$—$CHF_2$ or —$CF_2$—$CF_2$—$CH_2F$.

Halogen is fluorine, chlorine, bromine or iodine, preferably fluorine, chlorine or bromine, particularly preferably chlorine or bromine.

The term "triflate" refers to trifluoro-methanesulfonic acid ester or trifluoromethanesulfonate.

The term "nonaflate" refers to 1,1,2,2,3,3,4,4,4-nonafluoro-1-butanesulfonic acid ester or 1,1,2,2,3,3,4,4,4-nonafluoro-1-butanesulfonate.

The term "at least one of R1, R2, R3 or R4 are absent in case one or more of A1, A2, A3 or A4 are nitrogen atom," refers to a residue wherein the nitrogen atom is not substituted by any residue, e.g. in case A1 is nitrogen atom and A2, A3 and A4 are each a carbon atom and R4 is absent and R1, R2 and R3 are each a hydrogen atom the residue pyridine is formed. If R1, R2 and R3 are not each a hydrogen atom but one of the residues specified under b) to x) then a substituted pyridine residue is formed. In case A1 and A2 are each a nitrogen atom and A3 and A4 are each a carbon atom and R4 and R3 are absent and R1 and R2 are each a hydrogen atom the residue pyridazine is formed. If R1 and R2 are not each a hydrogen atom but one of the residues specified under b) to x) then a substituted pyridazine residue is formed.

Optically active carbon atoms present in the compounds of the formula (I) can independently of each other have R configuration or S configuration. The compounds of the formula (I) can be present in the form of pure enantiomers or pure diastereomers or in the form of mixtures of enantiomers and/or diastereomers, for example in the form of racemates. The present invention relates to pure enantiomers and mixtures of enantiomers as well as to pure diastereomers and mixtures of diastereomers. The invention comprises mixtures of two or of more than two stereoisomers of the formula (I), and it comprises all ratios of the stereoisomers in the mixtures. In case the compounds of the formula (I) can be present as E isomers or Z isomers (or cis isomers or trans isomers) the invention relates both to pure E isomers and pure Z isomers and to E/Z mixtures in all ratios. The invention also comprises all tautomeric forms of the compounds of the formula (I).

Diastereomers, including E/Z isomers, can be separated into the individual isomers, for example, by chromatography. Racemates can be separated into the two enantiomers by customary methods, for example by chromatography on chiral phases or by resolution, for example by crystallization of diastereomeric salts obtained with optically active acids or bases. Stereochemically uniform compounds of the formula (I) can also be obtained by employing stereochemically uniform starting materials or by using stereoselective reactions.

The starting materials or building blocks for use in the general synthetic procedures that can be applied in the preparation of the compounds of formula (I) are readily available to one of ordinary skill in the art. In many cases they are commercially available or have been described in the literature. Otherwise they can be prepared from readily available precursor compounds analogously to procedures described in the literature, or by procedures or analogously to procedures described in this application.

Furthermore, in order to obtain the desired substituents in the benzene nucleus and in the heterocyclic nucleus of the 2H-indazole or 2H-azaindazole ring system in the formula (I), the functional groups introduced into the ring system during the 2H-indazole or 2H-azaindazole synthesis can be chemically modified.

Especially the groups present in the 2H-indazole or 2H-azaindazole ring system can be modified by a variety of reactions and thus the desired residues R0, R1, R2, R3, R4 and R5 be obtained. For example, ester groups present in the benzene nucleus can be hydrolyzed to the corresponding carboxylic acids, which after activation can then be reacted with amines or alcohols under standard conditions. Ether groups present at the benzene nucleus, for example benzyloxy groups or other easily cleavable ether groups, can be cleaved to give hydroxyl groups which then can be reacted with a variety of agents, for example etherification agents or activating agents allowing replacement of the hydroxyl group by other groups. Sulfur-containing groups can be reacted analogously.

Due to the fact that in the present case the functional groups are attached to an 2H-indazole or 2H-azaindazole ring it may in certain cases become necessary to specifically adapt reaction conditions or to choose specific reagents from a variety of reagents that can in principle be employed into a conversion reaction, or otherwise to take specific measures for achieving a desired conversion, for example to use protection group techniques. However, finding out suitable reaction variants and reaction conditions in such cases does not cause any problems for one skilled in the art.

In the course of the preparation of the compounds of the formula I it can generally be advantageous or necessary to introduce functional groups which reduce or prevent undesired reactions or side reactions in the synthesis, in the form of precursor groups which are later converted into the desired functional groups, or to temporarily block functional groups by a protective group strategy suited to the synthesis problem. Such strategies are well known to those skilled in the art. As an example of a precursor group, cyan groups could be mentioned which in a later step can be transformed into carboxylic acid derivatives or by reduction into aminomethyl groups. Protective groups can also have the meaning of a solid phase, and cleavage from the solid phase stands for the removal of the protective group. The use of such techniques is known to those skilled in the art. For example, a phenolic hydroxyl group can be attached to a trityl-polystyrene resin, which serves as a protecting group, and the molecule is cleaved from this resin by treatment with TFA at a later stage of the synthesis.

In the course of the synthesis the employment of microwave assistance for speeding-up, facilitating or enabling reactions may be beneficial or even required in many cases. Some reactions are for example described by M. Larhed, A. Hallberg, Drug Discovery Today, 8 (2001) 406.

Physiologically tolerable salts of the compounds of formula I are non-toxic salts that are physiologically acceptable, in particular, pharmaceutically utilizable salts. Such salts of compounds of formula I containing acidic groups, for example, a carboxyl group (COOH), include, for example, alkali metal salts or alkaline earth metal salts, such as sodium salts, potassium salts, magnesium salts and calcium salts, as well as salts with physiologically tolerable quaternary ammonium ions, such as tetramethylammonium or tetraethylammonium, and acid addition salts with ammonia and physiologically tolerable organic amines, such as methylamine, dimethylamine, trimethylamine, ethylamine, triethylamine, ethanolamine or tris-(2-hydroxyethyl)amine. Basic groups contained in the compounds of formula I, for example, amino groups or guanidino groups, form acid addition salts, for example, with inorganic acids such as hydrochloric acid, hydrobromic acid, sulfuric acid, nitric acid or phosphoric acid, or with organic carboxylic acids and sulfonic acids such as formic acid, acetic acid, oxalic acid, citric acid, lactic acid, malic acid, succinic acid, malonic acid, benzoic acid, maleic acid, fumaric acid, tartaric acid, methanesulfonic acid or p-toluenesulfonic acid. Compounds of the formula I which simultaneously contain a basic group and an acidic group, for example, a guanidino group and a carboxyl group, can also be present as zwitterions (betaines) which are likewise included in the scope of the present invention.

Salts of compounds of formula I can be obtained by customary methods known to those skilled in the art, for example, by combining a compound of the formula I with an inorganic or organic acid or base in a solvent or dispersant, or from other salts by cation exchange or anion exchange. The present invention also includes all salts of the compounds of formula I which, because of low physiologically tolerability, are not directly suitable for use in pharmaceuticals but are suitable, for example, as intermediates for carrying out further chemical modifications of the compounds of formula I or as starting materials for the preparation of physiologically tolerable salts.

A further aspect of the invention is the use of a compound of the formula I as prepared by the process according to the invention for the production of pharmaceuticals, diagnostic agents, liquid crystals, polymers, herbicides, fungicidals, nematicidals, parasiticides, insecticides, acaricides and arthropodicides.

Preferred methods include, but are not limited to those described in the examples. Furthermore, the compounds of the formula I can be used as synthesis intermediates for the preparation of other compounds, in particular of other pharmaceutical active ingredients, which are obtainable from the compounds of the formula I, for example by introduction of substituents or modification of functional groups.

The general synthetic sequences for preparing the compounds useful in the present invention are outlined in the examples given below. Both an explanation of, and the actual procedure for, the various aspects of the present invention are described where appropriate. The following examples are intended to be merely illustrative of the present invention, and not limiting thereof in either scope or spirit. Those with skill in the art will readily understand that known variations of the conditions and processes described in the examples can be used to synthesize the compounds of the present invention.

EXAMPLES

When in the final step of the synthesis of a compound an acid such as trifluoroacetic acid or acetic acid was used, for example when trifluoroacetic acid was employed to remove a tBu group or when a compound was purified by chromatography using an eluent which contained such an acid, in some cases, depending on the work-up procedure, for example the details of a freeze-drying process, the compound was obtained partially or completely in the form of a salt of the acid used, for example in the form of the acetic acid salt or trifluoroacetic acid salt or hydrochloric acid salt.

| Abbreviations used: | |
|---|---|
| tert-Butyl | tBu |
| dibenzylidenacetone | dba |
| N,N-dimethylformamide | DMF |
| Ethylacetate | EtOAc |
| N-methylpyrrolidone | NMP |
| Fast atom bombardment | FAB |
| Liquid chromatography with mass spectrometry | LC-MS |
| Room temperature 21° C. to 24° C. | RT |
| Trifluoroacetic acid | TFA |

General procedure for the one-pot formation of 2H-indazoles from 2-haloacetylenes and monosubstituted hydrazines: To an oven dried reaction tube containing a magnic stirring bar was added the Pd source, ligand, solvent and base. The reaction tube was sealed with a septum and stirred for 30 min at RT under an inert atmosphere (nitrogen or argon) prior to addition of the reagents. The reagents were added and the mixture heated to desired temperature and reaction progress was followed by LCMS. Upon completion of the reaction as judged by LCMS, the reaction mixture was allowed to cool to RT and quenched with brine and extracted with EtOAc. The organic phase was dried over $Na_2SO_4$ followed by filtration, or by filtering through a Varian cartridge Chem Elut 12198007, before the solvent was removed by rotary evaporation and the residue purified by FC on silica using $CH_2Cl_2$/EtOAc or, in some cases $CH_2Cl_2$/MeOH. After rotary evaporation of the organic solvents, the desired 2H-indazole was obtained in high purity.

Example 1

3-Benzyl-2-phenyl-2H-indazole

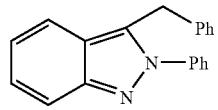

Following the general procedure outlined above, a reaction tube was charged with 4.4 mg $PdCl_2$ (5 mol %), 14.5 mg $tBu_3PHBF_4$ (10 mol %), 228.1 mg $Cs_2CO_3$ (1.4 equiv.) and 2.5 mL DMF. After stirring for 30 min at RT under a flow of argon, 1-chloro-2-phenylethynyl-benzene (106.3 mg, 1.0 equiv.) and phenylhydrazine (75.7 mg, 1.4 equiv.) were added and the reaction was heated to 130° C. for 3 hours. After cooling to RT, the reaction mixture was quenched with brine (30 mL) and extracted with EtOAc (2×30 mL) and the organic phase was dried by eluting through a Varian Chem Elut 12198007 cartridge. Removal of the solvents afforded the crude indazole as a dark-brown oil that purified by FC on silica using $CH_2Cl_2$/EtOAc to afford 115.0 mg (81%) of 3-benzyl-2-phenyl-2H-indazole colorless oil that solidified upon standing. $^1$H-NMR (DMSO-$d_6$) δ 4.47 (s, 2H), 6.98 (d, 2H, J=7.1 Hz), 7.03 (dd, 1H, J=7.9, 7.0 Hz), 7.13-7.24 (m, 3H), 7.30 (dd, 1H, J=8.1, 7.0 Hz), 7.52-7.58 (m, 5H), 7.60 (d, 1H, J=8.6 Hz), 7.65 (d, 1H, J=8.6 Hz); $^{13}$C-NMR (DMSO-$d_6$) δ 30.4, 117.1, 120.5, 121.0, 121.2, 125.9 (2C), 126.3, 126.4, 128.1 (2C), 128.4 (2C), 128.9, 129.2 (2C), 134.5, 137.9, 139.5, 147.9; HRMS (FAB): Calculated for $C_{20}H_{17}N_2$ (M+H$^+$) 285.1391, found 285.1385.

Example 2

The reaction was performed according to example 1 using 1-bromo-2-phenylethynyl-benzene (128.6 mg, 1.0 equiv.) instead of 1-chloro-2-phenylethynyl-benzene. The reaction afforded 112.2 mg (79%) 3-benzyl-2-phenyl-2H-indazole.

Example 3

The reaction was performed according to example 1 using 8.9 mg PdCl$_2$ (10 mol %), 29.0 mg tBu$_3$PHBF$_4$ (20 mol %) and 244.4 mg Cs$_2$CO$_3$ (1.5 equiv.) and a reaction temperature of 110° C. for 20 hours. The reaction afforded 106.5 mg (75%) 3-benzyl-2-phenyl-2H-indazole.

Example 4

The reaction was performed according to example 1 using 1.8 mg PdCl$_2$ (2 mol %) and 2.9 mg tBu$_3$PHBF$_4$ (4 mol %). The reaction afforded 105.1 mg (74%) 3-benzyl-2-phenyl-2H-indazole.

Example 5

The reaction was performed according to example 1 using 179.2 mg Cs$_2$CO$_3$ (1.1 equiv.). The reaction afforded 100.8 mg (71%) 3-benzyl-2-phenyl-2H-indazole.

Example 6

The reaction was performed according to example 1 using 22.9 mg Pd$_2$(dba)$_3$ (5 mol %), 29.0 mg tBu$_3$PHBF$_4$ (20 mol %) and 244.4 mg Cs$_2$CO$_3$ (1.5 equiv.) and a reaction temperature of 110° C. for 20 hours. The reaction afforded 105.1 mg (74%) 3-benzyl-2-phenyl-2H-indazole.

Example 7

The reaction was performed according to example 6 using dimethylacetamide (2.5 mL) as solvent. The reaction afforded 102.2 mg (72%) 3-benzyl-2-phenyl-2H-indazole.

Example 8

The reaction was performed according to example 6 using N-methylpyrrolidone (NMP, 2.5 mL) as solvent. The reaction afforded 108.0 mg (76%) 3-benzyl-2-phenyl-2H-indazole.

Example 9

The reaction was performed according to example 8 with a reaction temperature of 130° C. for 4 hours. The reaction afforded 109.3 mg (77%) 3-benzyl-2-phenyl-2H-indazole.

Example 10

The reaction was performed according to example 1 using 101.2 mg phenylhydrazine hydrochloride (1.4 equiv.) and 438.8 mg Cs$_2$CO$_3$ (2.7 equiv.). The reaction afforded 109.3 mg (77%) 3-benzyl-2-phenyl-2H-indazole.

Example 11

2-Phenyl-3-pyridin-2-ylmethyl-2H-indazole

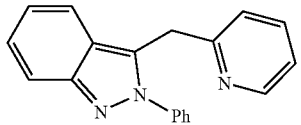

The reaction was performed according to example 1 using 106.8 mg 2-(2-chloro-phenylethynyl)-pyridine and a reaction temperature of 110° C. for 3 hours. This afforded 128.4 mg (90%) of the title compound. $^1$H-NMR (DMSO-$d_6$) δ 4.60 (s, 2H), 7.01 (ddd, 1H, J=8.5, 6.6, 0.7 Hz), 7.16 (d, 1H, J=7.9 Hz), 7.20 (ddd, 1H, J=7.4, 5.0, 0.9 Hz), 7.28 (ddd, 1H, J=8.8, 6.6, 1.2 Hz), 7.49-7.57 (m, 4H), 7.62-7.68 (m, 4H), 8.41 (d, J=5.0 Hz); $^{13}$C-NMR (DMSO-$d_6$) δ 33.3, 117.1, 120.6, 120.9, 121.4, 121.8, 122.8, 125.9, 126.4, 128.8, 129.1, 133.5, 136.8, 139.5, 147.9, 149.2, 157.5; HRMS (FAB): Calculated for $C_{19}H_{16}N_3$ (M+H$^+$) 286.1344, found 286.1337.

Example 12

2-Phenyl-3-(4-trifluoromethyl-benzyl)-2H-indazole

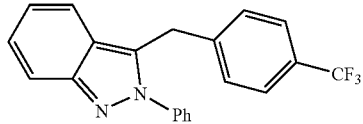

The reaction was performed according to example 1 using 140.3 mg 1-chloro-2-(4-trifluoromethylphenyl)ethynyl-benzene and a reaction temperature of 110° C. for 3 hours. This afforded 123.8 mg (83%) of the title compound. $^1$H-NMR (DMSO-$d_6$) δ 4.60 (s, 2H), 7.06 (dd, 1H, J=8.3, 6.7 Hz), 7.17 (d, 2H, J=8.0 Hz), 7.32 (dd, 1H, J=8.6, 6.8 Hz), 7.52-7.58 (m, 7H), 7.64 (d, 1H, J=7.4 Hz), 7.66 (d, 1H, J=8.0 Hz); $^{13}$C-NMR (DMSO-$d_6$) δ 30.1, 117.2, 120.4, 121.3, 125.2, 125.3, 125.9, 126.5, 127.1 (q, J=32.3 Hz, CF$_3$) 128.8, 129.0, 129.2, 133.5, 139.4, 142.7, 147.9.

Example 13

2-Phenyl-3-(4-methoxy-benzyl)-2H-indazole

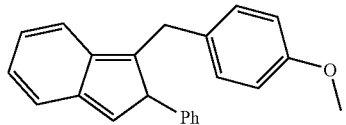

The reaction was performed according to example 1 using 121.3 mg 1-chloro-2-(4-methoxyphenyl)ethynyl-benzene and a reaction temperature of 110° C. for 3 hours. This afforded 135.2 mg (86%) of the title compound. $^1$H-NMR (DMSO-d$_6$) δ 3.67 (s, 3H), 4.39 (s, 2H), 6.77 (d, 2H, J=8.6 Hz) 6.89 (d, 2H, J=8.6 Hz), 7.02 (ddd, 1H, J=8.6, 6.5, 0.6 Hz), 7.28 (ddd, 1H, J=8.6, 6.7, 0.9 Hz), 7.52-7.59 (m, 6H), 7.63 (d, 1H, J=8.7 Hz); $^{13}$C-NMR (DMSO-d$_6$) δ 29.6, 54.9, 113.8, 117.1, 120.6, 120.9, 121.0, 125.9, 126.3, 128.8, 129.1, 129.2, 129.7, 134.9, 139.5, 147.9, 157.7; HRMS (FAB): Calculated for C$_{21}$H$_{19}$N$_2$O (M+H$^+$) 315.1497, found 315.1491.

Example 14

3-(6-Methoxy-naphthalen-2-ylmethyl)-2-phenyl-2H-indazole

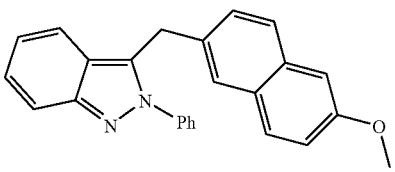

The reaction was performed according to example 1 using 146.4 mg 2-(2-chloro-phenylethynyl)-6-methoxy-naphthalene and a reaction temperature of 110° C. for 6 hours. This afforded 127.6 mg (70%) of the title compound. $^1$H-NMR (DMSO-d$_6$) δ 3.83 (s, 3H), 4.59 (s, 2H), 7.01 (ddd, 1H, J=8.4, 6.6, 0.6 Hz), 7.07-7.12 (m, 2H), 7.23 (d, 1H, J=2.4 Hz), 7.29 (ddd, 1H, J=8.7, 6.5, 0.9 Hz), 7.36 (s, 1H), 7.51-7.68 (m, 9H); ); $^{13}$C-NMR (DMSO-d$_6$) δ 30.5, 55.0, 105.7, 117.1, 118.7, 120.6, 121.0, 121.2, 125.9, 126.1, 126.4, 126.9, 127.1, 128.3, 128.5, 128.9, 129.1, 132.8, 132.9, 134.5, 139.5, 147.9, 157.0; HRMS (FAB): Calculated for C$_{25}$H$_{21}$N$_2$O (M+H$^+$) 365.1654, found 365.1648.

Example 15

N,N-Diisopropyl-2-(2-phenyl-2H-indazol-3-yl)-acetamide

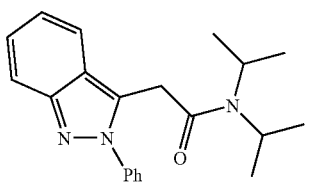

The reaction was performed according to example 1 using 131.9 mg 3-(2-chloro-phenyl)-propynoic acid diisopropylamide and at a reaction temperature of 110° C. for 2 hours. This afforded 105.5 mg (63%) of the title compound. $^1$H-NMR (DMSO-d$_6$) δ 1.01 (d, 6H, J=6.4 Hz), 1.15 (d, 6H, J=6.8 Hz), 3.38 (m, 1H), 3.96 (septet, 1H, J=6.8 Hz), 4.18 (s, 2H), 7.05 (ddd, 1H, J=8.6, 6.8, 1.0 Hz), 7.30 (ddd, 1H, J=8.6, 6.5, 0.9 Hz), 7.52-7.58 (m, 5H), 7.63 (d, 1H, J=8.7 Hz), 7.75 (d, 1H, J=8.7 Hz); $^{13}$C-NMR (DMSO-d$_6$) δ 20.1, 31.6, 44.8, 48.2, 116.9, 120.5, 120.6, 122.1, 125.5, 126.2, 128.6, 129.0, 131.4, 139.7, 147.8, 166.3; HRMS (FAB): Calculated for O$_{21}$H$_{26}$N$_3$O (M+H$^+$) 336.2075, found 336.2068.

Example 16

(2-Phenyl-2H-indazol-3-yl)-acetic acid tert-butyl ester

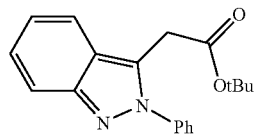

The reaction was performed according to example 1 using 118.4 mg (2-chloro-phenyl)-propynoic acid tert-butyl ester and a reaction temperature of 110° C. for 2 hours. This afforded 143.4 mg (93%) of the title compound. $^1$H-NMR (DMSO-d$_6$) 1.22 δ (s, 9H), 4.21 (s, 2H), 7.10 (ddd, 1H, J=8.3, 6.5, 0.6 Hz), 7.32 (ddd, 1H, J=8.6, 6.4, 0.9 Hz), 7.53-7.57 (m, 1H), 7.58-7.66 (m, 5H), 7.80 (d, 1H, J=8.6 Hz); $^{13}$C-NMR (DMSO-d$_6$) δ 27.3, 31.8, 80.8, 117.1, 120.4, 121.1, 121.8, 125.5, 126.5, 128.8, 129.2, 129.3, 139.5, 147.8, 167.8; HRMS (FAB): Calculated for C$_{19}$H$_{21}$N$_2$O$_2$ (M+H$^+$) 309.1603, found 309.1596.

Example 17

3-(2,2-Diethoxy-ethyl)-2-phenyl-2H-indazole

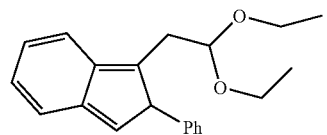

The reaction was performed according to example 1 using 119.4 mg 1-chloro-2-(3,3-diethoxy-prop-1-ynyl)-benzene. The reaction mixture was worked up by filtering through a short silicaplug to remove the base and catalyst using iPr$_2$O followed by evaporation of the solvents. The crude product was purified by FC on silica using CH$_2$Cl$_2$/EtOAc. This afforded 85.4 mg (55%) of the title compound. $^1$H-NMR (DMSO-d$_6$) δ 0.95 (t, 6H, J=7.1 Hz), 3.24-3.32 (m, 4H), 3.44-3.51 (m, 2H), 4.69 (t, 1H, J=5.5 Hz), 7.07 (ddd, 1H, J=8.3, 7.1, 0.6 Hz), 7.29 (ddd, 1H, J=8.7, 6.8, 0.9 Hz), 7.54-7.63 (m, 4H), 7.65-7.68 (m, 2H), 7.82 (d, 1H, J=8.6 Hz); $^{13}$C-NMR (DMSO-d$_6$) δ 14.9, 30.7, 61.9, 101.1, 117.0, 120.6, 121.1, 121.5, 126.3, 128.8, 129.1, 131.8, 139.7, 147.8; HRMS (FAB): Calculated for C$_{19}$H$_{23}$N$_2$O$_2$ (M+H$^+$) 311.1760, found 311.1754.

Example 18

3-(2,2-Dimethyl-propyl)-2-phenyl-2H-indazole

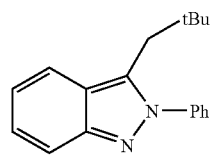

The reaction was performed according to example 1 using 96.4 mg 1-chloro-2-(3,3-dimethyl-but-1-ynyl)-benzene and a reaction time of 20 hours. This afforded 11.9 mg (9%) of the title compound. $^1$H-NMR (DMSO-d$_6$) δ 0.68 (s, 9H) 3.12 (s, 2H), 7.06 (dd, 1H, J=8.3, 6.8 Hz), 7.28 (dd, 1H, J=8.9, 7.6 Hz), 7.52-7.62 (m, 6H), 7.76 (d, 1H, J=8.6 Hz); $^{13}$C-NMR (DMSO-d$_6$) δ 29.5, 33.7, 37.1, 117.0, 120.6, 121.6, 122.1, 126.1, 126.7, 128.6, 129.1, 134.5, 140.4, 147.6.

Example 19

3-Hexyl-2-phenyl-2H-indazole

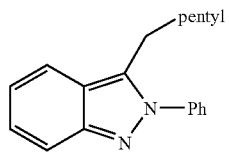

The reaction was performed according to example 1 using 103.4 mg 1-chloro-2-hept-1-ynyl-benzene and a reaction time of 20 hours. This afforded 15.3 mg (11%) of the title compound. $^1$H-NMR (DMSO-d$_6$) δ 0.78 (t, 3H, J=6.7 Hz, CH$_3$), 1.08-1.88 (m, 6H), 1.50 (quintet, 2H, J=7.1 Hz), 3.06 (t, 2H, J=7.6 Hz), 7.05 (dd, 1H, J=7.5, 7.4 Hz), 7.29 (dd, 1H, J=8.6, 6.6 Hz), 7.58-7.62 (m, 6H), 7.77 (d, 1H, J=8.6 Hz); $^{13}$C-NMR (DMSO-d$_6$) δ 13.7, 21.7, 24.2, 28.0, 28.3, 30.5, 117.0, 120.4, 120.5, 120.7, 125.9, 126.3, 128.8, 129.2, 136.4, 139.7, 147.7.

Example 20

3-Cyclopropylmethyl-2-phenyl-2H-indazole-6-carboxylic acid tert-butyl ester

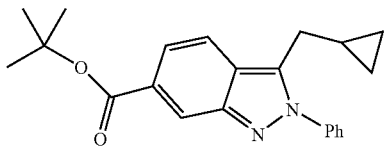

The reaction was performed according to example 1 using 138.4 mg 3-chloro-4-cyclopropylethynyl-benzoic acid tert-butyl ester and a reaction time of 4 hours. This afforded 81.9 mg (47%) of the title compound. $^1$H-NMR (DMSO-d$_6$) δ 0.10-0.15 (m 2H), 0.37-0.42 (m 2H), 0.86-0.94 (m, 1H), 1.59 (s, 9H), 3.01 (d, 2H, J=6.8 Hz), 7.54 (dd, 1H, J=8.9, 1.4 Hz), 7.58-7.68 (m, 5H), 7.96 (dd, 1H, J=8.9, 0.9 Hz), 8.25 (s, 1H); $^{13}$C-NMR (DMSO-d$_6$) δ 4.8, 10.2, 27.8, 29.2, 80.6, 119.8, 120.0, 121.3, 122.5, 126.1, 129.2, 129.3, 129.4, 136.9, 139.5, 146.9, 165.2.

Example 21

3-Benzyl-2-phenyl-2H-indazole-6-carboxylic acid tert-butyl ester

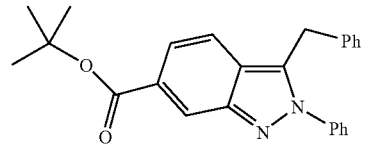

The reaction was performed according to example 1 using 156.4 mg 3-chloro-4-phenylethynyl-benzoic acid tert-butyl ester. This afforded 133.1 mg (69%) of the title compound. $^1$H-NMR (DMSO-d$_6$) δ 1.58 (s, 9H), 4.51 (s, 2H), 6.95 (d, 2H, J=7.6 Hz), 7.14-7.23 (m, 3H), 7.50 (dd, 1H, J=8.8, 1.3 Hz), 7.58 (br s, 5H), 7.68 (dd, 1H, J=8.8, 0.7 Hz), 8.28 (s, 1H); $^{13}$C-NMR (DMSO-d$_6$) δ 27.8, 30.4, 80.6, 115.1, 120.2, 120.9, 122.9, 125.8, 126.5, 128.1, 128.5, 129.3, 129.6, 135.3, 137.6, 139.2, 147.0, 165.2; HRMS (FAB): Calculated for C$_{25}$H$_{25}$N$_2$O$_2$ (M+H$^+$) 385.1916, found 385.1911.

Example 22

3-Cyclopentylmethyl-2-phenyl-2H-indazole-6-carboxylic acid tert-butyl ester

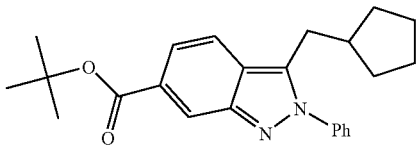

The reaction was performed according to example 1 using 152.4 mg 3-chloro-4-cyclopentylethenyl-benzoic acid tert-butyl ester and a reaction time of 4 hours. This afforded 17.3 mg (9%) of the title compound. $^1$H-NMR (DMSO-d$_6$) δ 0.98-1.08 (m, 2H), 1.33-1.40 (m, 2H), 1.41-1.49 (m, 4H), 1.59 (s, 9H), 1.99 (septet, 1H, J=7.5 Hz), 3.11 (d, 2H, J=7.6 Hz), 7.53 (dd, 1H, J=8.8, 1.3 Hz), 7.58-7.66 (m, 5H), 7.89 (d, 1H, J=8.8, 0.6 Hz), 8.24 (s, 1H); HRMS (FAB): Calculated for C$_{24}$H$_{28}$N$_2$O$_2$Na (M+Na$^+$) 399.2048, found 399.2045.

Example 23

Diethyl-[2-(2-phenyl-2H-indazol-3-yl)-ethyl]-amine

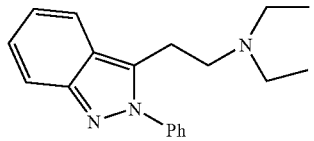

The reaction was performed according to example 1 using 110.9 mg [3-(2-chloro-phenyl)-prop-2-ynyl]-diethyl-amine and a reaction time of 20 hours. This afforded 44.0 mg (30%) of the title compound. $^1$H-NMR (DMSO-d$_6$) δ 0.76 (t, 6H, J=7.0 Hz), 2.34 (q, 4H, J=7.0 Hz), 2.56 (m, 2H), 3.16 (m, 2H), 7.06 (ddd, 1H, J=8.6, 6.5, 0.9 Hz), 7.29 (ddd, 1H, J=8.8, 6.5, 1.0 Hz), 7.55-7.66 (m, 6H), 7.77 (d, 1H, J=8.6 Hz); $^{13}$C-NMR (DMSO-d$_6$) δ 11.7, 22.4, 46.1, 51.0, 117.0, 120.4, 120.5, 120.9, 126.0, 126.3, 128.8, 129.1, 135.0, 139.7, 147.8; HRMS (FAB): Calculated for C$_{19}$H$_{24}$N$_3$ (M+H$^+$) 294.1970, found 294.1964.

Example 24

2-Phenyl-3-[2-(tetrahydro-pyran-2-yloxy)-ethyl]-2H-indazole

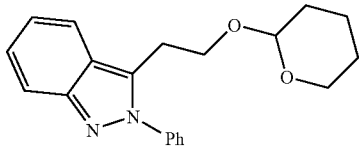

The reaction was performed according to example 1 using 125.4 mg 2-[3-(2-chloro-phenyl)-prop-2-ynyloxy]-tetrahydro-pyranat 100° C. for 2 hours. This afforded 37.1 mg (23%)

of the title compound. $^1$H-NMR (DMSO-d$_6$) δ 1.25-1.60 (m, 6H), 3.23-3.29 (m, 1H), 3.30-3.35 (m, 2H), 3.37-3.42 (m, 1H), 3.61 (dt, 1H, J=9.8, 6.8 Hz), 3.83 (dt, 1H, J=9.8, 6.5 Hz), 4.45 (m, 1H), 7.06 (ddd, 1H, J=8.6, 6.8, 0.9 Hz), 7.30 (ddd, 1H, J=9.0, 6.5, 0.9 Hz), 7.57 (d, 1H, J=7.1 Hz), 7.59-7.63 (m, 3H), 7.67 (d, 2H, J=8.6 Hz), 7.82 (d, 1H, J=8.3 Hz); $^{13}$C-NMR (DMSO-d$_6$) δ 18.8, 24.8, 25.6, 30.0, 60.9, 65.0, 97.6, 117.0, 120.6, 120.8, 121.1, 126.1, 126.3, 128.8, 129.1, 133.7, 139.6, 147.8.

Example 25

3-Benzyl-2-phenyl-5-trifluoromethyl-2H-indazole

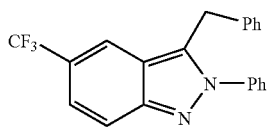

The reaction was performed according to example 1 using 140.3 mg 1-chloro-2-phenylethynyl-4-trifluoromethyl-benzene and a reaction time of 20 hours at 110° C. This afforded 107.5 mg (61%) of the title compound. $^1$H-NMR (DMSO-d$_6$) δ 4.58 (s, 2H), 6.97 (d, 2H, J=6.8 Hz), 7.15-7.24 (m, 3H), 7.51 (dd, 1H, J=9.0, 1.6 Hz), 7.58 (s, 5H), 7.85 (d, 1H, J=9.0 Hz), 8.08 (s, 1H); $^{13}$C-NMR (DMSO-d$_6$) δ 30.3, 118.8, 120.1 (q, J=5.0 Hz), 121.5, (q, J=30.5 Hz), 121.9, (q, J=2.5 Hz), 119.7, 125.9, 126.5, 128.2, 128.5, 129.2, 129.4, 137.3, 137.7, 139.1, 148.0; HRMS (FAB): Calculated for C$_{21}$H$_{16}$N$_2$F$_3$ (M+H$^+$) 353.1266, found 353.1261.

Example 26

3-Benzyl-6-fluoro-2-phenyl-2H-indazole

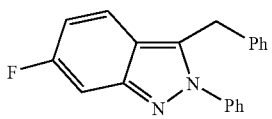

The reaction was performed according to example 1 using 115.3 mg 2-chloro-4-fluoro-1-phenylethynyl-benzene and a reaction time of 20 hours at 110° C. This afforded 64.4 mg (43%) of the title compound. $^1$H-NMR (DMSO-d$_6$) δ 4.47 (s, 2H), 6.92-6.99 (m, 3H), 7.14-7.23 (m, 3H), 7.37 (dd, 1H, J=10.4, 1.9 Hz), 7.53-7.58 (m, 5H), 7.66 (dd, 1H, J=9.2, 5.5 Hz); $^{13}$C-NMR (DMSO-d$_6$) δ 30.4, 100.1 (d, J=23.5 Hz), 112.3 (d, J=27.8 Hz), 118.6, 123.1 (d, J=11.0 Hz), 125.8, 126.5, 128.1, 128.5, 129.0, 129.2, 135.6, 137.6, 139.3, 147.5, 147.6, 161.2 (d, J=241.7 Hz); HRMS (FAB): Calculated for C$_{20}$H$_{16}$N$_2$F (M+H$^+$) 303.1297, found 303.1292.

Example 27

3-Benzyl-4-methyl-2-phenyl-2H-indazole

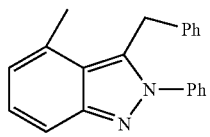

The reaction was performed according to example 1 using 113.4 mg 1-chloro-3-methyl-2-phenylethynyl-benzene and a reaction time of 4 hours at 110° C. This afforded 95.8 mg (64%) of the title compound. $^1$H-NMR (DMSO-d$_6$) δ 2.40 (s, 3H), 4.53 (s, 2H), 6.78 (d, 1H, J=6.4 Hz), 6.91 (d, 2H, J=7.2 Hz), 7.15-7.21 (m, 2H), 7.22-7.27 (m, 2H), 7.45-7.55 (m, 6H); $^{13}$C-NMR (DMSO-d$_6$) δ 19.2, 30.9, 115.0, 120.8, 121.4, 126.0, 126.3, 126.5, 127.3, 128.6, 129.0, 129.1, 131.0, 133.9, 139.0, 139.3, 148.4; HRMS (FAB): Calculated for C$_{21}$H$_{19}$N$_2$ (M+H$^+$) 299.1548, found 299.1543.

Example 28

3-Benzyl-6-methoxy-2-phenyl-2H-indazole

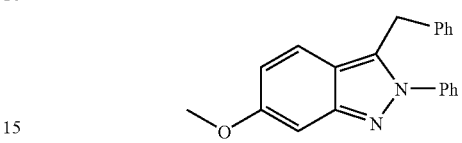

The reaction was performed according to example 1 using 121.4 mg 2-chloro-4-methoxy-1-phenylethynyl-benzene and a reaction time of 4 hours at 130° C. This afforded 114.5 mg (73%) of the title compound. $^1$H-NMR (DMSO-d$_6$) δ 3.81 (s, 3H), 4.43 (s, 2H), 6.68 (dd, 1H, J=9.0, 2.0 Hz), 6.93 (d, 1H, J=2.0 Hz), 6.96 (d, 2H, J=7.1 Hz), 7.44 (d, 1H, J=9.0 Hz), 7.48-7.57 (m, 5H); $^{13}$C-NMR (DMSO-d$_6$) δ 30.4, 55.0, 94.2, 115.9, 117.0, 121.4, 125.7, 126.4, 128.0, 128.4, 128.5, 129.1, 134.5, 137.9, 139.6, 148.9, 158.6; HRMS (FAB): Calculated for C$_{21}$H$_{19}$N$_2$O (M+H$^+$) 315.1497, found 315.1491.

Example 29

3-Benzyl-5-methoxy-2-phenyl-2H-indazole

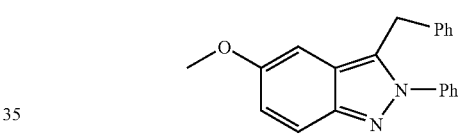

The reaction was performed according to example 1 using 121.4 mg 1-chloro-4-methoxy-2-phenylethynyl-benzene and a reaction time of 5 hours at 110° C. This afforded 98.7 mg (63%) of the title compound. $^1$H-NMR (DMSO-d$_6$) δ 3.72 (s, 3H), 4.44 (s, 2H), 6.89 (d, 1H, J=2.2 Hz), 6.96-6.99 (m, 3H), 7.14-7.18 (m, 1H), 7.19-7.23 (m, 2H), 7.49-7.54 (m, 4H), 7.56 (d, 1H, J=9.0 Hz); $^{13}$C-NMR (DMSO-d$_6$) δ 30.3, 55.1, 96.8, 118.7, 121.2, 121.3, 125.6, 126.3, 128.1, 128.4, 128.6, 129.1, 133.1, 138.1, 139.7, 144.8, 154.1; HRMS (FAB): Calculated for C$_{21}$H$_{19}$N$_2$O (M+H$^+$) 315.1497, found 315.1491.

Example 30

Toluene-4-sulfonic acid 3-benzyl-2-phenyl-2H-indazol-6-yl ester

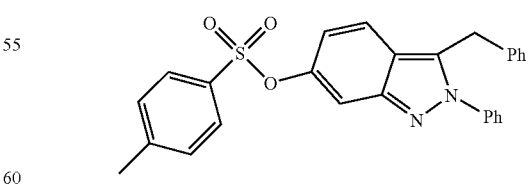

The reaction was performed according to example 1 using 191.4 mg toluene-4-sulfonic acid 3-chloro-4-phenylethynyl-phenyl ester and a reaction time of 4 hours at 110° C. This afforded 80.7 mg (36%) of the title compound. $^1$H-NMR (DMSO-d$_6$) δ 2.42 (s, 3H), 4.44 (s, 2H), 6.72 (dd, 1H, J=8.9, 1.9 Hz), 6.94 (d, 2H, J=6.9 Hz), 7.13-7.21 (m, 4H), 7.48 (d, 2H, J=8.1 Hz), 7.51-7.58 (m, 5H), 7.61 (d, 1H, J=8.9 Hz), 7.80 (d, 2H, J=8.3 Hz); $^{13}$C-NMR (DMSO-d$_6$) δ 21.1, 30.3, 109.1, 116.8, 119.7, 122.7, 125.9, 126.5, 128.1, 128.2, 128.5, 129.2, 130.2, 131.6, 135.7, 137.4, 139.1, 145.7, 146.9, 147.8; HRMS (FAB): Calculated for C$_{27}$H$_{23}$N$_2$O$_3$S (M+H$^+$) 455.1429, found 455.1429.

Example 31

3-Benzyl-2-phenyl-2H-indazole-5-carboxylic acid

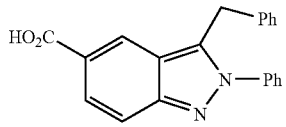

The reaction was performed according to example 1 using 128.3 mg 4-chloro-3-phenylethynyl-benzoic acid and a reaction time of 4 hours at 110° C. The reaction was purified by preparative RP HPLC using MeCN/H$_2$O/TFA as eluent. This afforded 75.6 mg (46%) of the title compound. $^1$H-NMR (DMSO-d$_6$) δ 4.55 (s, 2H), 6.98 (d, 1H, J=7.2 Hz), 7.15-7.24 (m, 3H), 7.58 (br s, 5H), 7.69 (d, 1H, J=9.0 Hz), 7.81 (d, 1H, J=9.0 Hz), 8.36 (s, 1H); $^{13}$C-NMR (DMSO-d$_6$) δ 30.4, 117.1, 120.6, 123.6, 125.0, 125.9, 126.2, 126.5, 128.1, 128.5, 129.3, 137.5, 137.6, 139.1, 148.9, 167.5; HRMS (FAB): Calculated for C$_{21}$H$_{17}$N$_2$O$_2$ (M+H$^+$) 329.1290, found 329.1286.

Example 32

3-Benzyl-2-phenyl-2H-pyrazolo[4,3-c]pyridine

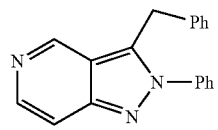

The reaction was performed according to example 1 using 156.4 mg 4-chloro-3-phenylethynyl-pyridine and a reaction time of 3 hours at 110° C. This afforded 24.0 mg (17%) of the title compound. $^1$H-NMR (DMSO-d$_6$) δ 4.56 (s, 2H), 7.06 (dd, 2H, J=7.6, 1.5 Hz), 7.18-7.28 (m, 3H), 7.55 (dd, 1H, J=6.3, 1.2 Hz), 7.61 (br s, 5H), 8.21 (d, 1H, J=6.3 Hz), 8.91 (d, 1H, J=1.1 Hz); $^{13}$C-NMR (DMSO-d$_6$) δ 30.7, 110.6, 117.0, 126.1, 126.7, 128.4, 128.6, 129.3, 129.5, 137.1, 137.7, 138.9, 142.0, 147.7, 148.4.

Example 33

3-Benzyl-2-(4-methoxy-phenyl)-2H-indazole

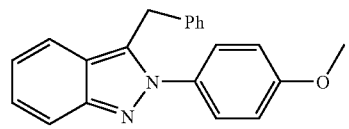

The reaction was performed according to example 1 using 122.2 mg 4-methoxyphenylhydrazine hydrochloride, 439.9 mg Cs$_2$CO$_3$ (2.7 equiv.) and a reaction time of 4 hours at 130° C. This afforded 125.0 mg (80%) of the title compound. $^1$H-NMR (DMSO-d$_6$) δ 3.33 (s, 3H), 4.43 (s, 2H), 6.97-7.02 (m, 3H), 7.09 (d, 2H, J=8.6 Hz), 7.17 (d, 1H, J=7.4 Hz), 7.21 (d, 2H, J=7.6 Hz), 7.28 (ddd, 1H, J=8.6, 6.7, 1.0 Hz), 7.45 (d, 2H, J=8.6 Hz), 7.56 (d, 1H, J=8.4 Hz), 7.61 (d, 1H, J=8.6 Hz); $^{13}$C-NMR (DMSO-d$_6$) δ 30.4, 55.4, 114.2, 117.0, 120.4, 120.8, 121.0, 126.2, 126.3, 127.1, 128.0, 128.4, 132.4, 134.4, 137.9, 147.6, 159.3; HRMS (FAB): Calculated for C$_{21}$H$_{19}$N$_2$O (M+H$^+$) 315.1497, found 315.1491.

Example 34

3-Benzyl-2-(4-fluoro-phenyl)-2H-indazole

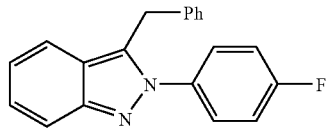

The reaction was performed according to example 1 using 113.8 mg 4-fluorophenylhydrazine hydrochloride, 439.9 mg Cs$_2$CO$_3$ (2.7 equiv.) and a reaction time of 3 hours at 130° C. This afforded 128.8 mg (85%) of the title compound. $^1$H-NMR (DMSO-d$_6$) δ 4.46 (s, 2H), 6.97 (d, 2H, J=6.7 Hz), 7.03 (ddd, 1H, J=8.5, 6.6, 0.9 Hz), 7.13-7.23 (m, 3H), 7.30 (ddd, 1H, J=8.8, 6.6, 1.2 Hz), 7.36-7.42 (m, 2H), 7.57-7.65 (m, 4H); $^{13}$C-NMR (DMSO-d$_6$) δ 30.3, 116.0 (d, J=23.1 Hz), 117.1, 120.5, 121.1 (d, J=8.0 Hz), 126.4, 126.5, 128.1, 128.2, 128.4, 134.8, 135.9 (d, J=3.0 Hz), 137.7, 147.8, 161.8 (d, J=246.3 Hz); HRMS (FAB): Calculated for C$_{20}$H$_{16}$N$_2$F (M+H$^+$) 303.1297, found 303.1292.

Example 35

3-Benzyl-2-(2-fluoro-phenyl)-2H-indazole

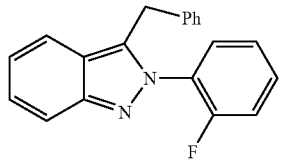

The reaction was performed according to example 1 using 113.8 mg 2-fluorophenyl-hydrazine hydrochloride, 439.9 mg Cs$_2$CO$_3$ (2.7 equiv.) and a reaction time of 5 hours at 130° C. This afforded 123.0 mg (81%) of the title compound. $^1$H-NMR (DMSO-d$_6$) δ 4.33 (s, 2H), 6.92 (d, 2H, J=6.7 Hz), 7.05 (ddd, 1H, J=8.2, 6.5, 0.9 Hz), 7.12-7.21 (m, 3H), 7.31 (ddd, 1H, J=8.6, 6.6, 0.9 Hz), 7.40 (dd, 1H, J=7.6, 0.9 Hz), 7.49 (ddd, 1H, J=8.6, 8.2, 1.2 Hz), 7.57 (ddd, 1H, J=8.2, 7.8, 1.6 Hz), 7.61-7.66 (m, 3H); $^{13}$C-NMR (DMSO-d$_6$) δ 30.2, 116.6 (d, J=19.5 Hz), 117.1, 120.4, 120.5, 121.1, 125.0 (d, J=3.7 Hz), 126.4, 126.6, 127.1 (d, J=12.0 Hz), 128.1, 128.3, 129.4, 131.8 (d, J=8.2 Hz), 136.3, 137.3, 148.3, 156.3 (d, J=250.6 Hz); HRMS (FAB): Calculated for $C_{20}H_{16}N_2F$ (M+H$^+$) 303.1297, found 303.1292.

Example 36

4-(3-Benzyl-indazol-2-yl)-benzonitrile

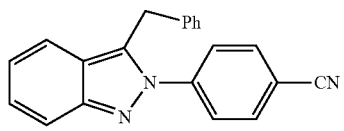

The reaction was performed according to example 1 using 118.7 mg 4-cyanophenylhydrazine hydrochloride, 439.9 mg $Cs_2CO_3$ (2.7 equiv.) and a reaction time of 3 hours at 130° C. This afforded 143.3 mg (93%) of the title compound. $^1$H-NMR (DMSO-d$_6$) δ 4.56 (s, 2H), 6.97 (d, 2H, J=7.0 Hz), 7.05 (dd, 1H, J=8.4, 6.8 Hz), 7.16 (d, 1H, J=7.0 Hz), 7.19-7.23 (m, 2H), 7.32 (ddd, 1H, J=8.7, 6.6, 0.9 Hz), 7.60 (d, 1H, J=8.6 Hz), 7.65 (d, 1H, J=8.8 Hz), 7.82 (d, 2H, J=8.6 Hz), 8.04 (d, 2H, J=8.6 Hz); $^{13}$C-NMR (DMSO-d$_6$) δ 30.3, 111.3, 117.2, 118.1, 120.7, 121.5, 121.7, 126.5, 126.6, 127.0, 128.1, 128.5, 133.4, 135.1, 137.5, 143.1, 148.4; HRMS (FAB): Calculated for $C_{21}H_{16}N_3$ (M+H$^+$) 310.1344, found 310.1340.

Example 37

3-Benzyl-2-naphthalen-1-yl-2H-indazole

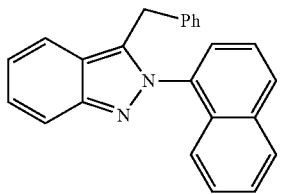

The reaction was performed according to example 1 using 118.7 mg 1-naphthylhydrazine hydrochloride, 439.9 mg $Cs_2CO_3$ (2.7 equiv.) and a reaction time of 4 hours at 130° C. This afforded 105.7 mg (63%) of the title compound. $^1$H-NMR (DMSO-d$_6$) δ 4.21 (br s, 2H), 6.83 (d, 2H, J=7.5 Hz), 6.91 (d, 1H, J=8.6 Hz), 7.04-7.11 (m, 4H), 7.34 (dd, 1H, J=6.6, 8.1 Hz), 7.43 (ddd, 1H, J=8.1, 6.8, 1.2 Hz), 7.57-7.63 (m, 2H), 7.65-7.70 (m, 3H), 8.09 (d, 1H, J=8.2 Hz), 8.09 (d, 1H, J=8.2 Hz), 8.19 (d, 1H, J=8.4 Hz); $^{13}$C-NMR (DMSO-d$_6$) δ 30.5, 117.2, 120.3, 120.6, 121.0, 122.3, 125.1, 125.4, 126.2, 126.4, 126.7, 127.5, 128.0, 128.1, 128.2, 129.5, 129.9, 133.4, 135.5, 136.6, 137.4, 148.0; HRMS (FAB): Calculated for $C_{24}H_{19}N_2$ (M+H$^+$) 335.1548, found 335.1548.

Example 38

3-Benzyl-2-pyridin-4-yl-2H-indazole

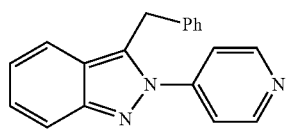

The reaction was performed according to example 1 using 101.9 mg 4-hydrazino-pyridine hydrochloride, 439.9 mg $Cs_2CO_3$ (2.7 equiv.) and a reaction time of 3 hours at 130° C. This afforded 134.6 mg (94%) of the title compound. $^1$H-NMR (DMSO-d$_6$) δ 4.64 (s, 2H), 7.00 (d, 2H, J=7.1 Hz), 7.06 (ddd, 1H, J=8.4, 6.5, 0.7 Hz), 7.15-7.18 (m, 1H), 7.20-7.24 (m, 2H), 7.33 (ddd, 1H, J=8.6, 6.5, 0.9 Hz), 7.61 (d, 1H, J=8.5 Hz), 7.66 (d, 1H, J=8.6 Hz), 7.68-7.71 (m, 2H), 8.74-8.76 (m, 2H); $^{13}$C-NMR (DMSO-d$_6$) δ 30.3, 117.3, 119.6, 120.7, 121.6, 122.0, 126.5, 127.2, 128.1, 128.5, 135.0, 137.5, 146.3, 148.5, 150.9; HRMS (FAB): Calculated for $C_{19}H_{16}N_3$ (M+H$^+$) 286.1344, found 286.1339.

Example 39

4-(3-Benzyl-indazol-2-yl)-quinoline

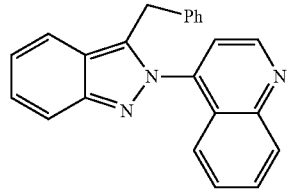

The reaction was performed according to example 1 using 137.0 mg 4-hydrazinoquinoline hydrochloride, 439.9 mg $Cs_2CO_3$ (2.7 equiv.) and a reaction time of 3 hours at 130° C. This afforded 74.9 mg (45%) of the title compound. $^1$H-NMR (DMSO-d$_6$) δ 4.35 (s, 2H), 6.80-6.84 (m, 2H), 7.00-7.05 (m, 3H), 7.13 (dd, 1H, J=8.5, 6.7 Hz), 7.18 (d, 1H, J=8.4 Hz), 7.38 (dd, 1H, J=6.8, 7.4 Hz), 7.52 (dd, 1H, J=8.4, 7.2 Hz), 7.70-7.7.76 (m, 3H), 7.83 (dd, 1H, J=6.8, 8.5 Hz), 8.18 (d, 1H, J=8.5 Hz), 9.11 (d, 1H, J=4.6 Hz); $^{13}$C-NMR (DMSO-d$_6$) δ 30.3, 117.2, 119.6, 120.6, 120.7, 121.5, 123.0, 124.0, 126.3, 127.0, 127.9, 128.1, 128.2, 129.1, 130.3, 136.9, 137.2, 143.2, 148.5, 148.7, 150.5.

Example 40

3-Benzyl-2-pyridin-4-yl-2H-indazole-6-carboxylic acid tert-butyl ester

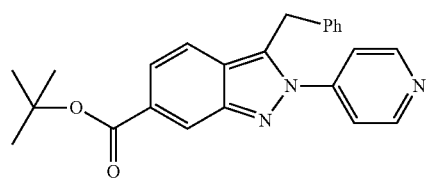

The reaction was performed according to example 1 using 156.4 mg 3-chloro-4-phenylethynyl-benzoic acid tert-butyl ester, 101.9 mg 4-hydrazinopyridine hydrochloride (1.4 equiv.) and 456.2 mg $Cs_2CO_3$ (2.8 equiv.) with a reaction time of 2 hours at 110° C. This afforded 104.7 mg (54%) of the title compound. $^1$H-NMR (DMSO-d$_6$) δ 1.58 (s, 9H), 4.66 (s, 2H), 6.98 (d, 2H, J=7.4 Hz), 7.15-7.24 (m, 3H), 7.51 (dd, 1H, J=8.8, 1.3 Hz), 7.69-7.73 (m, 3H), 8.30 (s, 1H), 8.77 (dd, 2H, J=4.6, 1.6 Hz); HRMS (FAB): Calculated for $C_{24}H_{24}N_3O_2$ (M+H$^+$) 386.1869, found 386.1864.

Example 41

3-Cyclopropylmethyl-2-pyridin-4-yl-2H-indazole-6-carboxylic acid tert-butyl ester

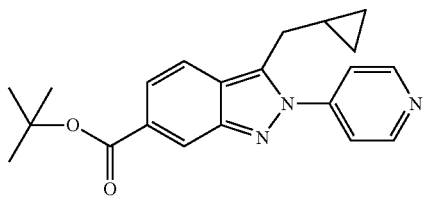

The reaction was performed according to example 1 using 138.4 mg 3-chloro-4-cyclopropylethynyl-benzoic acid tert-butyl ester, 101.9 mg 4-hydrazinopyridine hydrochloride (1.4 equiv.) and 456.2 mg $Cs_2CO_3$ (2.8 equiv.) with a reaction time of 4 hours at 110° C. This afforded 73.0 mg (42%) of the title compound. $^1$H-NMR (DMSO-$d_6$) δ 0.14-0.18 (m, 2H), 0.40-0.45 (m, 2H), 0.91-1.00 (m, 1H), 1.59 (s, 9H), 3.16 (d, 2H, J=6.8 Hz), 7.54 (dd, 1H, J=8.9, 1.3 Hz), 7.81 (dd, 2H, J=4.5, 1.6 Hz), 7.99 (dd, 1H, J=8.9, 0.8 Hz), 8.85 (dd, 2H, J=4.5, 1.6 Hz); HRMS (FAB): Calculated for $C_{21}H_{24}N_3O_2$ (M+H$^+$) 350.1869, found 350.1864.

Example 42

3-Benzyl-2-methyl-2H-indazole

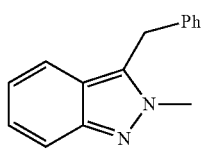

The reaction was performed according to example 1 using 32.3 mg methylhydrazine with a reaction time of 5 hours at 110° C. This afforded 68.6 mg (62%) of the title compound. $^1$H-NMR (DMSO-$d_6$) δ 4.03 (s, 3H), 4.48 (s, 2H), 6.96 (dd, 1H, J=8.2, 6.5 Hz), 7.17-7.24 (m, 4H), 7.28-7.33 (m, 2H), 7.51 (d, 1H, J=8.5 Hz), 7.57 (d, 1H, J=8.5 Hz); $^{13}$C-NMR (DMSO-$d_6$) δ 29.6, 37.6, 116.6, 120.0, 120.2, 120.8, 125.3, 126.4, 128.3, 128.6, 133.8, 137.8, 146.9; HRMS (FAB): Calculated for $C_{15}H_{15}N_2$ (M+H$^+$) 223.1235, found 223.1231.

Example 43

3-Benzyl-2-phenethyl-2H-indazole

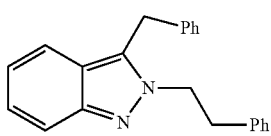

The reaction was performed according to example 1 using 95.3 mg phenethylhydrazine with a reaction time of 20 hours at 110° C. This afforded 77.7 mg (50%) of the title compound. $^1$H-NMR (DMSO-$d_6$) δ 3.01 (t, 2H, J=7.6 Hz), 4.29 (s, 2H), 4.51 (t, 2H, J=7.6 Hz), 6.95 (ddd, 1H, J=8.2, 6.5, 0.6 Hz), 7.07 (d, 2H, J=7.0 Hz), 7.11 (d, 2H, J=7.0 Hz), 7.19-7.31 (m, 7H), 7.51 (d, 1H, J=8.5 Hz), 7.56 (d, 1H, J=8.5 Hz); $^{13}$C-NMR (DMSO-$d_6$) δ 29.3, 35.9, 51.0, 116.7, 120.1, 120.2, 120.6, 125.4, 126.4, 126.7, 128.2, 128.3, 128.6, 128.7, 133.7, 137.9, 138.0, 147.2; HRMS (FAB): Calculated for $C_{22}H_{21}N_2$ (M+H$^+$) 313.1705, found 313.1698.

Example 44

3-Benzyl-2-isopropyl-2H-indazole

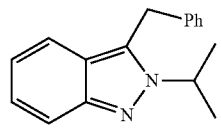

The reaction was performed according to example 1 using 77.4 mg isopropylhydrazine hydrochloride, 439.9 mg $Cs_2CO_3$ (2.7 equiv.) and a reaction time of 20 hours at 110° C. This afforded 68.4 mg (55%) of the title compound. $^1$H-NMR (DMSO-$d_6$) δ 1.35 (d, 6H, J=6.6 Hz), 4.50 (s, 2H), 4.86 (septet, 1H, J=6.6 Hz), 6.97 (ddd, 1H, J=8.3, 6.5, 0.6 Hz), 7.16-7.23 (m, 4H), 7.27-7.32 (m, 2H), 7.56 (d, 1H, J=8.6 Hz), 7.64 (d, 1H, J=8.6 Hz); $^{13}$C-NMR (DMSO-$d_6$) δ 22.6, 29.2, 50.3, 116.9, 120.0, 120.1, 120.6, 125.2, 126.4, 128.1, 128.5, 132.4, 138.3, 147.0; HRMS (FAB): Calculated for $C_{17}H_{19}N_2$ (M+H$^+$) 251.1548, found 251.1542.

Example 45

3-Benzyl-2-cyclohexyl-2H-indazole

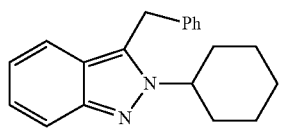

The reaction was performed according to example 1 using 105.5 mg cyclohexyl-hydrazine hydrochloride, 439.9 mg $Cs_2CO_3$ (2.7 equiv.) and a reaction time of 20 hours at 110° C. This afforded 69.4 mg (48%) of the title compound. $^1$H-NMR (DMSO-$d_6$) δ 1.13-1.40 (m, 3H), 1.63 (br t, 3H, J=13.0 Hz), 1.74 (d, 2H, J=13.4, Hz), 1.89 (dq, 2H, J=3.4, 12.6 Hz), 4.45 (tt, 1H, J=3.6, 11.4 Hz), 4.50 (s, 2H), 6.96 (ddd, 1H, J=8.3, 6.5, 0.7 Hz), 7.16-7.23 (m, 4H), 7.26-7.32 (m, 2H), 7.54 (d, 1H, J=8.7 Hz), 7.65 (d, 1H, J=8.5 Hz); $^{13}$C-NMR (DMSO-$d_6$) δ 24.8, 24.9 (2C), 29.3, 32.8, 57.7, 116.9, 120.0, 120.1, 120.4, 125.1, 126.4, 128.2, 128.5, 132.7, 138.5, 146.9; HRMS (FAB): Calculated for $C_{20}H_{23}N_2$ (M+H$^+$) 291.1861, found 291.1856.

Example 46

3-Benzyl-2-thiophen-2-ylmethyl-2H-indazole-6-carboxylic acid tert-butyl ester

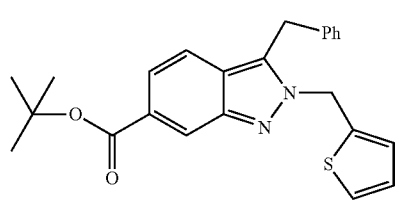

The reaction was performed according to example 1 using 156.4 mg 3-chloro-4-phenylethynyl-benzoic acid tert-butyl ester, 164.7 mg thiophen-2-ylmethyl-hydrazine hydrochloride (2.0 equiv.) and 488.7 mg Cs$_2$CO$_3$ (3.0 equiv.) with a reaction time of 5 hours at 110° C. This afforded 72.8 mg (36%) of the title compound. $^1$H-NMR (DMSO-d$_6$) δ 1.56 (s, 9H), 4.58 (s, 2H), 5.86 (s, 2H), 6.93 (dd, 1H, J=5.1, 3.5 Hz), 7.04 (dd, 1H, J=3.5, 1.0 Hz), 7.16 (d, 2H, J=7.4 Hz), 7.20-7.29 (m, 3H), 7.42 (dd, 1H, J=8.8, 1.2 Hz), 7.44 (dd, 1H, J=5.0, 1.2 Hz), 7.55 (dd, 1H, J=8.7, 0.7 Hz), 8.20 (s, 1H).

The invention claimed is:
1. A process for preparing a compound of formula I

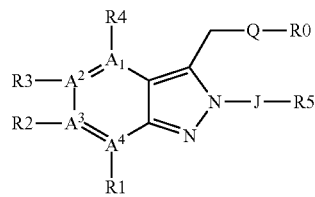

and/or all stereoisomeric forms of the compound of formula I, and/or mixtures of these forms in any ratio, and/or a physiologically tolerated salt of the compound of formula I, wherein;
A1, A2, A3 and A4 form together with the two carbon atoms in formula I form a benzene,
Q is a covalent bond,
—(C$_1$-C$_6$)-alkylene,
—(C$_3$-C$_6$)-cycloalkyl,
phenyl, wherein phenyl is unsubstituted or mono-, di-, tri- or four times substituted independently of one another by R13;
—(C$_1$-C$_4$)-alkylene-O—(C$_1$-C$_4$)-alkylene,
—(C$_1$-C$_4$)-alkylene-O—; or
—(C$_5$-C$_{14}$)-heteroaryl is selected from pyridyl, quinolinyl, tetrahydropyranyl and thienyl,
J is a covalent bond, —(C$_1$-C$_6$)-alkylene, —(C$_3$-C$_6$)-cycloalkyl, phenyl, naphthyl, or —(C$_5$-C$_{14}$)-heteroaryl, wherein heteroaryl is as defined above,
R0, R1, R2, R3 and R4 are independent of one another identical or different and are a) hydrogen atom,
b) —(C$_1$-C$_4$)-alkyl, wherein alkyl is unsubstituted or substituted one, two or three times by R13,
c) F, Cl or Br,
d) naphthyl, wherein naphthyl is unsubstituted or substituted one, two or three times by R13,
e) phenyl, wherein phenyl is unsubstituted or substituted one, two or three times by R13,
f) —(C$_5$-C$_{14}$)-heteroaryl, wherein heteroaryl is as defined above,
g) —(C$_3$-C$_6$)-cycloalkyl,
h) —O—(C$_1$-C$_4$)-alkyl,
i) —CN,
j) —OH,
k) —C(O)—R10,
l) —C(O)—O—R11,
m) —C(O)—N(R11)-R12,
n) —N(R11)-R12, or
p) —O—SO$_2$—R13,
R5 is a) —(C$_1$-C$_4$)-alkyl, wherein alkyl is unsubstituted or substituted one, two or three times by R13,
b) F, Cl or Br,
c) naphthyl, wherein naphthyl is unsubstituted or substituted one, two or three times by R13,
d) phenyl, wherein phenyl is unsubstituted or substituted one, two or three times by R13,
e) —(C$_5$-C$_{14}$)-heteroaryl, wherein heteroaryl is as defined above,
f) —(C$_3$-C$_6$)-cycloalkyl,
g) —O—(C$_1$-C$_4$)-alkyl,
h) —CN,
i) —OH,
j) —C(O)—R10,
k) —C(O)—R11,
l) —C(O)—N(R11)-R12,
m) —N(R11)-R12, or
n) —O—SO$_2$—R13,
R10 is hydrogen atom or —(C$_1$-C$_4$)-alkyl,
R11 and R12 are independently of one another identical or different and are hydrogen atom or —(C$_1$-C$_4$)-alkyl, wherein alkyl is unsubstituted or mono-, di- or trisubstituted independently of one another by R13,
R13 is F, Cl, —CN, —OH, —(C$_1$-C$_4$)-alkoxy, —CF$_3$ or phenyl, wherein phenyl is unsubstituted or mono-, di- or trisubstituted independently of one another by R14,
R14 is F, Cl, —OH, —CN, —CF$_3$, —(C$_1$-C$_4$)-alkyl or —(C$_1$-C$_4$)-alkoxy, said process comprises reacting a compound of formula II

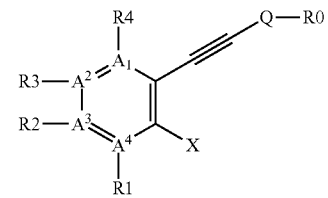

wherein R0, R1, R2, R3, R4, A1, A2, A3, A4 and Q are as defined in formula I and X is Cl, Br, I or tosylate,
with a compound of formula III or any salts thereof,

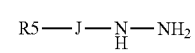

wherein J and R5 are as defined in formula I,
in the presence of a transition metal catalyst selected from the group Pd-halides, Pd-halide complexes, Pd-phosphine complexes and Pd-alkene complexes to give a compound of formula I and
optionally the compound of formula I is converted to its physiologically tolerated salt; wherein the compounds of formula I prepared are selected from the group consisting of: 3-Benzyl-2-phenyl-2H-indazole; 2-Phenyl-3-pyridin-2-ylmethyl-2H-indazole; 2-Phenyl-3-(4-trifluoromethyl-benzyl)-2H-indazole; 2-Phenyl-3-(4-methoxy-benzyl)-2H-indazole; 3-(6-Methoxy-naphthalen-2-ylmethyl)-2-phenyl-2H-indazole; N,N-Diisopropyl-2-(2-phenyl-2H-indazol-3-yl)-acetamide; (2-Phenyl-2H-indazol-3-yl)-acetic acid tert-butyl ester; 3-(2,2-Diethoxy-ethyl)-2-phenyl-2H-indazole; 3-(2,2-Dimethyl-propyl)-2-phenyl-2H-indazole; 3-Hexyl-2-phenyl-2H-indazole; 3-Cyclopropylmethyl-2-phenyl-2H-indazole-6-carboxylic acid tert-butyl ester; 3-Benzyl-2-phenyl-2H-indazole-6-carboxylic acid tert-butyl ester; 3-Cyclopentylmethyl-2-phenyl-2H-indazole-6-carboxylic acid tert-butyl ester; Diethyl-[2-(2-phenyl-2H-indazol-3-yl)-ethyl]-amine; 2-Phenyl-3-[2-(tetrahydro-pyran-2-yloxy)-ethyl]-2H-indazole; 3-Benzyl-2-phenyl-5-trifluoromethyl- 2H-indazole; 3-Benzyl-6-fluoro-2-phenyl-2H-indazole; 3-Benzyl-4-methyl-2-phenyl-2H-indazole; 3-Benzyl-6-methoxy-2-phenyl-2H-indazole; 3-Benzyl-5-methoxy-2-phenyl-2H-indazole; Toluene-4-sulfonic acid 3-benzyl-2-phenyl-2H-indazol-6-yl ester; 3-Benzyl-2-phenyl-2H-indazole-5-carboxylic acid; 3-Benzyl-2-phenyl-2H-pyrazolo[4,3-c]pyridine; 3-Benzyl-2-(4-methoxy-phenyl)-2H-indazole; 3-Benzyl-2-(4-fluoro-phenyl)-2H-indazole; 3-Benzyl-2-(2-fluoro-phenyl)-2H-indazole; 4-(3-Benzyl-indazol-2-yl)-benzonitrile; 3-Benzyl-2-naphthalen-1-yl-2H-indazole; 3-Benzyl-2-pyridin-4-yl-2H-indazole; 4-(3-Benzyl-indazol-2-yl)-quinoline; 3-Benzyl-2-pyridin-4-yl-2H-indazole-6-carboxylic acid tert-butyl ester; 3-Cyclopropylmethyl-2-pyridin-4-yl-2H-indazole-6-carboxylic acid tert-butyl ester; 3-Benzyl-2-methyl-2H-indazole; 3-Benzyl-2-phenethyl-2H-indazole; 3-Benzyl-2-isopropyl-2H-indazole; 3-Benzyl-2-cyclohexyl-2H-indazole and 3-Benzyl-2-thiophen-2-ylmethyl-2H-indazole-6-carboxylic acid tert-butyl ester.

\* \* \* \* \*